United States Patent
Jester et al.

(10) Patent No.: US 9,558,323 B2
(45) Date of Patent: Jan. 31, 2017

(54) SYSTEMS AND METHODS FOR WORKFLOW MODIFICATION THROUGH METRIC ANALYSIS

(71) Applicant: General Electric Company, Schenectady, NY (US)

(72) Inventors: Eric Jester, Hoffman Estates, IL (US); Madhu Seepani, Lake In The Hills, IL (US); Mark Niggemann, Palatine, IL (US); Charlotte Mae Shelton, Gilbert, AZ (US); Rhonda Eckstein, Baileyton, AL (US)

(73) Assignee: General Electric Company, Schenectady, NY (US)

( * ) Notice: Subject to any disclaimer, the term of this patent is extended or adjusted under 35 U.S.C. 154(b) by 76 days.

(21) Appl. No.: 14/091,812

(22) Filed: Nov. 27, 2013

(65) Prior Publication Data

US 2015/0149193 A1    May 28, 2015

(51) Int. Cl.
 *G06Q 50/22* (2012.01)
 *G06Q 10/06* (2012.01)
 *G06F 19/00* (2011.01)

(52) U.S. Cl.
 CPC .................. *G06F 19/327* (2013.01)

(58) Field of Classification Search
 CPC ........ G06Q 50/22; G06Q 50/24; G06Q 10/06; G06Q 10/0631; G06Q 10/06311; G06Q 10/063116; G06Q 10/1097; G06F 19/327
 See application file for complete search history.

(56) References Cited

U.S. PATENT DOCUMENTS

| | | | |
|---|---|---|---|
| 7,970,634 B2 | 6/2011 | Backhaus et al. | |
| 2003/0149598 A1 | 8/2003 | Santoso et al. | |
| 2004/0019501 A1 | 1/2004 | White et al. | |
| 2004/0249676 A1 | 12/2004 | Marshall et al. | |
| 2006/0053035 A1 | 3/2006 | Eisenberg | |
| 2006/0143060 A1 | 6/2006 | Conry et al. | |

(Continued)

OTHER PUBLICATIONS

Burke et al., "The State of the Art of Nurse Rostering," Journal of Scheduling, 2004, pp. 441-499, vol. 7, Kluwer Academic Publishers, the Netherlands, (59 pages).

(Continued)

*Primary Examiner* — Joseph Burgess
(74) *Attorney, Agent, or Firm* — Hanley, Flight & Zimmerman, LLC

(57) ABSTRACT

An example system to manage a radiologist workflow includes a first interface to monitor a distribution status of at least one medical exam. The medical exam is to be at least one of automatically allocated or assigned to an examiner work queue based on one or more rules. The example system includes a second interface to view at least one metric associated with distribution of the at least one medical exam and an assignment tool to be displayed via the first interface. The assignment tool is to facilitate assignment of the medical exam to an examiner work queue. The example system includes a rules viewer to be displayed via a third interface. The rules viewer is to facilitate configuration of the one or more rules based on the distribution status, the at least one metric, or the assignment. The rules viewer is to automatically update the one or more rules.

21 Claims, 13 Drawing Sheets

(56) References Cited

U.S. PATENT DOCUMENTS

| | | | |
|---|---|---|---|
| 2006/0195339 A1* | 8/2006 | Backhaus | G06F 19/327 705/2 |
| 2006/0212317 A1 | 9/2006 | Hahn et al. | |
| 2007/0073556 A1 | 3/2007 | Lau et al. | |
| 2007/0143136 A1 | 6/2007 | Moore, III et al. | |
| 2007/0179831 A1* | 8/2007 | Patnaik | G06Q 10/0631 705/7.16 |
| 2007/0226008 A1 | 9/2007 | Halsted et al. | |
| 2009/0240529 A1 | 9/2009 | Chess et al. | |
| 2009/0287500 A1 | 11/2009 | Benjamin et al. | |
| 2009/0313046 A1 | 12/2009 | Badgett et al. | |
| 2011/0066449 A1 | 3/2011 | Backhaus et al. | |
| 2011/0113329 A1 | 5/2011 | Pusateri | |
| 2011/0125539 A1 | 5/2011 | Bollapragada et al. | |
| 2012/0096385 A1 | 4/2012 | Bank et al. | |
| 2012/0116816 A1 | 5/2012 | Smith | |
| 2012/0226719 A1 | 9/2012 | Sewall | |
| 2013/0018674 A1* | 1/2013 | Bedi et al. | 705/3 |
| 2013/0132105 A1 | 5/2013 | Wood-Salomon et al. | |
| 2013/0132142 A1* | 5/2013 | Wood-Salomon et al. | 705/7.15 |
| 2013/0151284 A1 | 6/2013 | Cohen-Solal et al. | |
| 2013/0218592 A1 | 8/2013 | Hashmat | |
| 2015/0066529 A1 | 3/2015 | Latuca et al. | |
| 2015/0149192 A1 | 5/2015 | Jester et al. | |
| 2015/0149206 A1 | 5/2015 | Jester et al. | |

OTHER PUBLICATIONS

Dang et al., "An ontological knowledge framework for adaptive medical workflow," Journal of Biomedical Informatics, 2008, pp. 829-836, vol. 41, Knowledge Management, Siemens Corporate Research, Princeton, NJ, (8 pages).

Mack et al., "New Aspects of Image Distribution and Workflow in Radiology," Journal of Digital Imaging, May 2000, pp. 17-21, vol. 13 No. 2, W.B. Saunders Company, Witten, Germany, (5 pages).

Meyer et al., "A Database Program for the Management of Staff Scheduling in a Radiology Department," Presented at the annual meeting of the Society for Pediatric Radiology, St. Louis, May 1997, American Journal of Roentgenology, pp. 1489-1492, vol. 169 (Dec. 1997), American Roentgen Ray Society, (4 pages).

Naidu et al., "Managing Personnel through Staff Scheduling Algorithms," Proceedings of the Fifth Joint Conference on Information Sciences, 2000, pp. 829-835, vol. 5 No. 2, Duke University, Durham, NC, (7 pages).

Welter et al., "Workflow management of content-based image retrieval for CAD support in PACS environments based on IHE," International Journal for Computer Assisted Radiology and Surgery, published Apr. 9, 2010, pp. 393-400, vol. 5, Aachen University Hospital, Aachen, Germany, (8 pages).

United States Patent and Trademark Office, "Non-Final Office Action," issued in connection with U.S. Appl. No. 14/091,769 on Aug. 31, 2015, 23 pages.

United States Patent and Trademark Office, "Final Office Action," issued in connection with U.S. Appl. No. 14/091,769 on May 9, 2016, 28 pages.

United States Patent and Trademark Office, "Non-Final Office Action," issued in connection with U.S. Appl. No. 14/091,801 on Feb. 18, 2016, 22 pages.

United States Patent and Trademark Office, "Advisory Action," issued in connection with U.S. Appl. No. 14/091,769 on Jul. 29, 2016, 14 pages.

United States Patent and Trademark Office, "Final Office Action," issued in connection with U.S. Appl. No. 14/091,801 on Sep. 9, 2016, 21 pages.

United States Patent and Trademark Office, "Non-Final Office Action," issued in connection with U.S. Appl. No. 14/091,769 on Oct. 14, 2016, 21 pages.

\* cited by examiner

FIG. 3

INTELLIGENT WORK ALLOCATION CONCEPT

[EVALUATE] [RESET] [EXPORT]                                    [HOME] [ADMIN] [SIMULATOR] [VIEWER]

SCORECARDS                                                 [HOME]

DRAG A COLUMN HEADER AND DROP IT HERE TO GROUP BY THAT COLUMN              [SEARCH]

| | PATIENT | CRITICAL | ASSIGNED | ALLOCATED | QUEUED | BODY PART | RADIOLOGIST | SLA EXPIRATION |
|---|---|---|---|---|---|---|---|---|
| ASSIGN | LANDSBERRY, THELMA ALI (302) | ○ | ○ | ● (308) | ○ | LEG | (316) | 8/20/2013 11:55:58 AM |
| ASSIGN | MATEO, SHIELO | ○ | ○ | ○ | ○ | UPPER EXTREMITY | | 8/20/2013 12:00:19 AM |
| ASSIGN | TAYLOR, RYAN | ○ | ○ | ○ | ○ | UPPER EXTREMITY | | 8/20/2013 1:02:38 AM |
| ASSIGN | CRAMER, BONIE | ○ (304) | ○ (306) | ○ | ○ | HEAD | | 8/20/2013 1:09:53 AM |
| ASSIGN | DREAREE, DANIEL | ● | ● | ○ | ● (310) | UPPER EXTREMITY | | 8/20/2013 1:11:48 AM |
| ASSIGN | MATTSON, CATHERIENE | ○ | ○ | ● | ○ | THORAX | JACKSON, LOVITA | 8/20/2013 09:55:50 AM |

300 / 126 / 318

INTELLIGENT WORK ALLOCATION CONCEPT

[EVALUATE] [RESET] [EXPORT] [SEARCH]  [HOME] [ADMIN] [SIMULATOR] [VIEWER]

DRAG A COLUMN HEADER AND DROP IT HERE TO GROUP BY THAT COLUMN

| | PATIENT | ALLOCATED | MODALITY | BODY PART | RADIOLOGIST | RVU |
|---|---|---|---|---|---|---|
| ASSIGN | LANDSBERRY, THELMA ALI | ● | CR | LEG | | 4 |
| ASSIGN | MATEO, SHIELD | ○ | CR | UPPER EXTREMITY | | 4 |
| ASSIGN | TAYLOR, RYAN | ○ | CT | UPPER EXTREMITY | | 4 |
| ASSIGN | GAGE, JAMES | ○ | VA | LEG | CASEY, BEN | 3 |
| ASSIGN | DREAREE, DANIEL | ○ | CT | UPPER EXTREMITY | | 4 |
| ASSIGN | MATTSON, CATHERIENE | ● | US | THORAX | JACKSON, LOVITA | 1 |

SCORECARDS

BEN CASEY ● ONLINE STATUS

| STAFF MEMBER | SPECIALTY | TOTAL | RVU |
|---|---|---|---|
| CASER, BEN | 0 | 0 | 0 |
| JONES, LEAH | 0 | 0 | 0 |
| LATTA, MICHAEL | 0 | 0 | 0 |
| STEWART, CHRIS | 0 | 0 | 0 |
| JANOFF, ROBIN | 0 | 0 | 0 |
| JOHNSON, JHON | 0 | 0 | 0 |

SYSTEMS AND METHODS FOR WORKFLOW MODIFICATION THROUGH METRIC ANALYSIS

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored can include patient medication orders, medical histories, imaging data, test results, diagnosis information, management information, and/or scheduling information, for example.

Medical exam results stored in, for example, the radiology information system, require review by an examining radiologist. Distribution of the exams for review by the radiologist involves consideration of various factors, including, for example, radiologist workloads, exam characteristics, available resources, and/or hospital efficiency goals. Such considerations are often present across a network of radiologists, hospitals, and/or institutions. Efforts to manage exam distribution in view of institutional work flow goals can be time-consuming, inefficient, and result in inequities with respect to the distribution of the medical exams for review. Further, hospital administrators lack efficient tools for managing radiologist workflows, analyzing metrics associated with the distribution of exams, and dynamically implementing workflow modifications based on the metric analysis.

BRIEF SUMMARY

Certain examples provide methods, systems, and machine readable storage devices or storage discs for managing radiologist workflows. Certain examples provide a system to manage radiologist workflow. The example system includes a first interface to monitor a distribution status of at least one medical exam. The medical exam is to be at least one of automatically allocated or assigned to an examiner work queue based on one or more rules. The example system includes a second interface to view at least one metric associated with distribution of the at least one medical exam. The example system includes an assignment tool to be displayed via the first interface. The assignment tool is to facilitate assignment of the medical exam to an examiner work queue. The example system includes a rules viewer to be displayed via a third interface. The rules viewer is to facilitate configuration of the one or more rules based on the distribution status, the at least one metric, or the assignment. In the example system, the rules viewer to automatically update the one or more rules.

Certain examples provide a method for monitoring radiologist workflow. The example method includes monitoring a distribution status of at least one medical exam via a first interface. In the example method, the medical exam is to be at least one of automatically allocated or assigned to an examiner work queue based on one or more rules. The example method includes displaying at least one metric associated with the distribution of the at least one medical exam via a second interface. The example method includes facilitating an assignment of the medical exam to an examiner work queue via the first interface. The example method also includes facilitating a configuration of the one or more rules based on the distribution status, the at least one metric, or the assignment via the first interface. The example method includes automatically updating the one or more rules.

Certain examples provide a machine readable storage device or storage disc storing instruction thereon, which, when read, cause a machine to at least monitor a distribution status of at least one medical exam via a first interface. The medical exam is to be at least one of automatically allocated or assigned to an examiner work queue based on one or more rules. The example instructions cause the machine to display at least one metric associated with the distribution of the at least one medical exam via a second interface. The example instructions also cause the machine to facilitate an assignment of the medical exam to an examiner work queue via the first interface. The example instructions cause the machine to facilitate a configuration of the one or more rules based on the distribution status, the at least one metric, or the assignment via the first interface. The example instructions also cause the machine to automatically update the one or more rules.

BRIEF DESCRIPTION OF SEVERAL VIEWS OF THE DRAWINGS

FIG. 3 illustrates an example first screen of an example graphical user interface associated with the example medical exam distributor of FIG. 1.

FIG. 3b illustrates a second view of the example first screen of FIG. 3.

FIG. 5 illustrates an example third screen of the example graphical user interface associated with the example medical exam distributor of FIG. 1.

Figure 1:
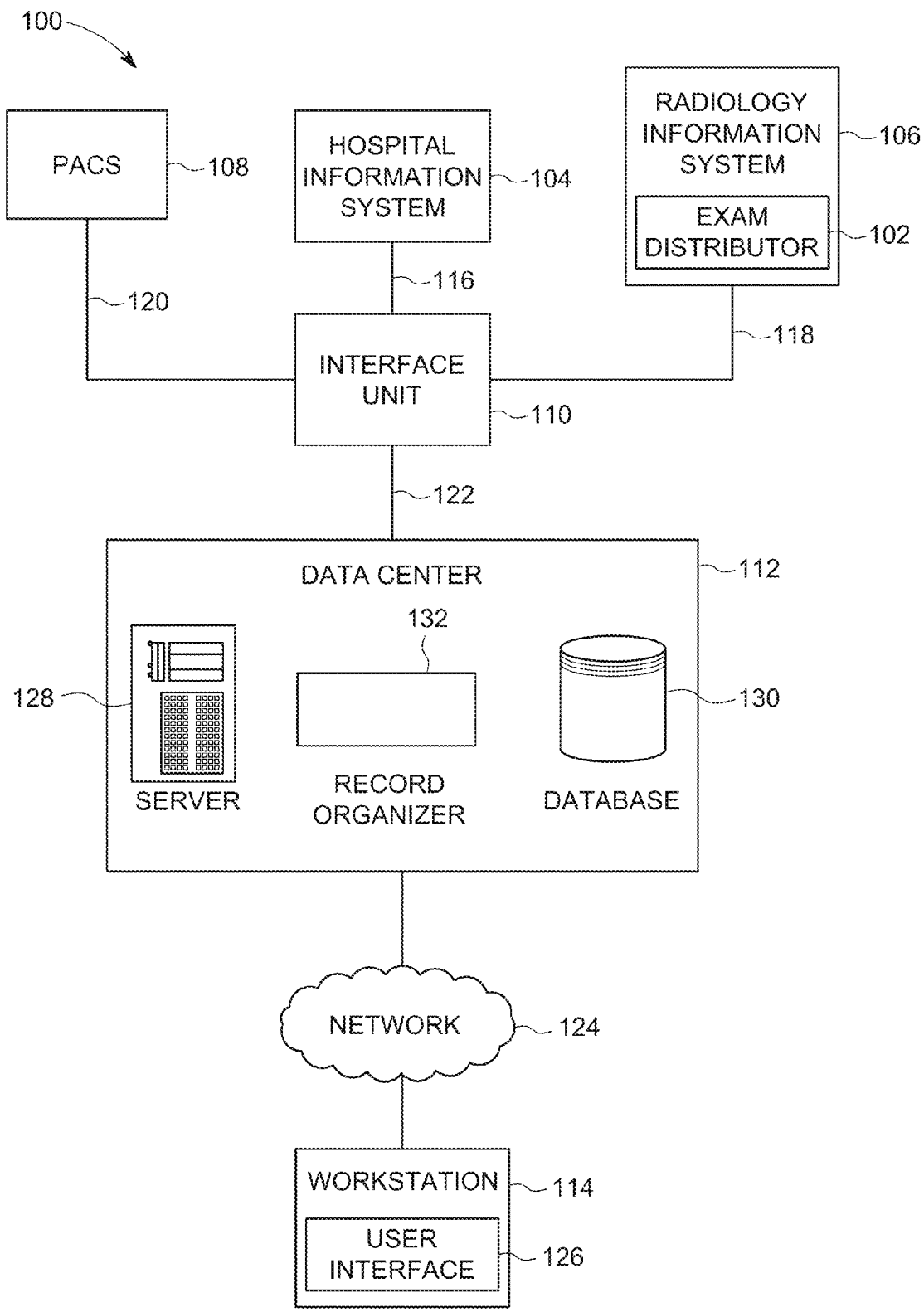
FIG. 1 is a block diagram of an example medical exam distributor in an example healthcare system.

The foregoing summary, as well as the following detailed description of certain examples of the present disclosure, will be better understood when read in conjunction with the appended drawings. For the purpose of illustrating the disclosure, certain examples are shown in the drawings. Wherever possible, the same reference numbers will be used throughout the drawing(s) and accompanying written description to refer to the same or like parts. It should be understood, however, that the present disclosure is not limited to the arrangements and instrumentality shown in the attached drawings.

DETAILED DESCRIPTION OF CERTAIN EXAMPLES

Although the following discloses example methods, systems, and machine readable storage devices and storage discs including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, and machine readable storage devices and storage discs, the examples provided are not the only way to implement such methods, systems, and machine readable storage devices and storage discs.

Also, although the methods, systems and machine readable storage mediums disclosed here are described in regards to healthcare applications, including, but not limited to, radiology information systems, it is to be understood that the present methods, systems and machine readable storage mediums can also be used to distribute information in any other industry/application.

A medical exam conducted on a patient can involve review by a healthcare practitioner to obtain, for example, diagnostic information from the exam. In a hospital setting, medical exams can be ordered for a plurality of patients, all of which require review by an examining practitioner. Each exam has associated attributes, such as a modality, a part of the human body under exam, and/or an exam priority level related to a patient criticality level. Hospital administrators, in managing distribution of exams for review by practitioners, can consider the exam attributes as well as staff availability, staff credentials, and/or institutional factors such as service level agreements and/or overhead costs. Balancing practitioner workloads in view of the exams requiring review can involve time-consuming efforts that result in inefficiencies and/or inequities in exam distribution across a network of practitioners. Further, some practitioners habitually decline to review and/or select to review exams having certain attributes. Load-balancing rules that automatically allocate exams to practitioners while allowing for a user, such as an administrator and/or a practitioner, to review the allocation and control assignment of the exams provide for efficient management of practitioner workloads in view of hospital workflow goals and clinical targets.

Additionally, an administrator may wish to view metrics or statistics associated with the distribution and review status of exams across the network, hospital, and/or institution. Such metrics can relate to, for example, radiologist performance, exam review efficiency, revenues, and/or whether certain contractual targets with respect to exam review have been met. In some examples, the administrator seeks to implement changes to the workflow allocation based on a review of the metrics. A system that generates current and historical operational statistics associated with exam distribution and allows for the administrator to dynamically influence workload allocation outcomes provides for a data-driven approach to workflow efficiency. Further, a system that automatically optimizes workflow allocation based on the current and historical data as well as inherent characteristics of the healthcare environment provides for a responsive approach to exam distribution and shared workload management in view of institutional goals.

Disclosed herein are example systems, methods, and machine readable storage devices and storage discs that provide for management of the distribution of medical exams to examining practitioners. The disclosed example systems, methods, and machine readable storage devices and storage discs can be used as part of a radiology information system to oversee the distribution of radiology medical exams to radiologists for review. The examples disclosed herein include graphical user interfaces accessible by one or more administrators of a radiology network, institution (e.g., a hospital), and/or group of institutions to review, influence, and/or improve workflow allocation. The examples disclosed herein also include an optimizer to automatically monitor the workflow allocation, evaluate user feedback via the graphical user interfaces, and implement process improvements directed toward increases workflow efficiency.

The disclosed example graphical user interfaces facilitate management of workload allocation across a network by providing for an administrator to view real-time information about the distribution statuses of exams requiring review by a radiologist. For example, the administrator can monitor the allocation and/or assignment status of exams to radiologist work queues. The administrator can also view one or more exam characteristics via the graphical user interfaces, including, for example, an amount of time allocated for reviewing the exam based on contractual agreements with healthcare insurance providers. Additionally, the example graphical user interfaces facilitate administrative review of network- and/or institutional-level operational statistics. In generating both real-time and historical operational statistics, the example graphical user interfaces enable the administrator to analyze exam distribution outcomes in view of workflow targets. In further examples, the example graphical user interfaces provide for the administrator to adjust the workflow allocation by revising one or more parameters defining the load-balancing rules. In some examples, the administrator can enact the parameter updates at a radiologist-level and/or across the radiologist network. Changes implemented by the administrator to, for example, radiologist workflows via the example user interfaces described herein are dynamically reflected across graphical user interfaces viewable by the radiologists in the network.

Examples disclosed herein also facilitate automated improvements or optimizations to the load-balancing rules based on current and historical data collected from ongoing monitoring of exam distribution and user feedback. Examples disclosed herein provide for analysis of the exam distribution data with a view toward improving the allocation process and increasing efficiency in workflow management. In dynamically generating and implementing improvements during the exam distribution process, examples disclosed herein provide for a responsive, analytical approach to workflow allocation.

Turning now to the figures, FIG. 1 shows a block diagram of an example healthcare system 100 capable of implementing an example medical exam distributor 102. The example healthcare system 100 includes the example medical exam distributor 102, a hospital information system (HIS) 104, a radiology information system (RIS) 106, a picture archiving and communication system (PACS) 108, an interface unit 110, a data center 112, and a workstation 114. In the illustrated example, the HIS 104, the RIS 106, and the PACS 108 are housed in a healthcare facility and locally archived. However, in other implementations, the HIS 104, the RIS 106, and/or the PACS 108 can be housed one or more other suitable locations. In certain implementations, one or more of the PACS 108, RIS 106, HIS 104, etc., can be implemented remotely via a thin client and/or downloadable software solution. Furthermore, one or more components of the healthcare system 100 can be combined and/or implemented together. For example, the RIS 106 and/or the PACS 108 can be integrated with the HIS 104; the PACS 108 can be integrated with the RIS 106; and/or the three example information systems 104, 106, and/or 108 can be integrated together. In other example implementations, the healthcare system 100 includes a subset of the illustrated information systems 104, 106, and/or 108. For example, the healthcare system 100 can include only one or two of the HIS 104, the RIS 106, and/or the PACS 108. Information (e.g., scheduling, test results, exam image data, observations, diagnosis, etc.) can be entered into the HIS 104, the RIS 106, and/or the PACS 108 by healthcare practitioners (e.g., radiologists, physicians, and/or technicians) and/or administrators before and/or after patient examination.

The HIS 104 stores medical information such as clinical reports, patient information, and/or administrative information received from, for example, personnel at a hospital, clinic, and/or a physician's office. The RIS 106 stores information such as, for example, radiology reports, radiology exam image data, messages, warnings, alerts, patient scheduling information, patient demographic data, patient tracking information, and/or physician and patient status monitors. Additionally, the RIS 106 enables exam order entry (e.g., ordering an x-ray of a patient) and image and film tracking (e.g., tracking identities of one or more people that have checked out a film). In some examples, information in the RIS 106 is formatted according to the HL-7 (Health Level Seven) clinical communication protocol. In certain examples, the medical exam distributor 102 is located in the RIS 106 to facilitate distribution of radiology exams to a radiologist workload for review and management of the exam distribution by, for example, an administrator. In an alternative example, the exam distributor 102 can be located separately or can be included in any other suitable device of the healthcare system 100.

The PACS 108 stores medical images (e.g., x-rays, scans, three-dimensional renderings, etc.) as, for example, digital images in a database or registry. In some examples, the medical images are stored in the PACS 108 using the Digital Imaging and Communications in Medicine ("DICOM") format. Images are stored in the PACS 108 by healthcare practitioners (e.g., imaging technicians, physicians, radiologists) after a medical imaging of a patient and/or are automatically transmitted from medical imaging devices to the PACS 108 for storage. In some examples, the PACS 108 can also include a display device and/or viewing workstation to enable a healthcare practitioner or provider to communicate with the PACS 108.

The interface unit 110 includes a hospital information system interface connection 116, a radiology information system interface connection 118, a PACS interface connection 120, and a data center interface connection 122. The interface unit 110 facilities communication among the HIS 104, the RIS 106, the PACS 108, and/or the data center 112. The interface connections 116, 118, 120, and 122 can be implemented by, for example, a Wide Area Network ("WAN") such as a private network or the Internet. Accordingly, the interface unit 110 includes one or more communication components such as, for example, an Ethernet device, an asynchronous transfer mode ("ATM") device, an 802.11 device, a DSL modem, a cable modem, a cellular modem, etc. In turn, the data center 112 communicates with the workstation 114, via a network 124, implemented at a plurality of locations (e.g., a hospital, clinic, doctor's office, other medical office, or terminal, etc.). The network 124 is implemented by, for example, the Internet, an intranet, a private network, a wired or wireless Local Area Network, and/or a wired or wireless Wide Area Network. In some examples, the interface unit 110 also includes a broker (e.g., a Mitra Imaging's PACS Broker) to allow medical information and medical images to be transmitted together and stored together.

The interface unit 110 receives images, medical reports, administrative information, exam workload distribution information, and/or other clinical information from the information systems 104, 106, 108 via the interface connections 116, 118, 120. If necessary (e.g., when different formats of the received information are incompatible), the interface unit 110 translates or reformats (e.g., into Structured Query Language ("SQL") or standard text) the medical information, such as medical reports, to be properly stored at the data center 112. The reformatted medical information can be transmitted using a transmission protocol to enable different medical information to share common identification elements, such as a patient name or social security number. Next, the interface unit 110 transmits the medical information to the data center 112 via the data center interface connection 122. Finally, medical information is stored in the data center 112 in, for example, the DICOM format, which enables medical images and corresponding medical information to be transmitted and stored together.

The medical information is later viewable and easily retrievable at the workstation 114 (e.g., by their common identification element, such as a patient name or record number). The workstation 114 can be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstation 114 receives commands and/or other input from a user via, for example, a keyboard, mouse, track ball, microphone, etc. The workstation 114 is capable of implementing a user interface 126 to enable a healthcare practitioner and/or administrator to interact with the healthcare system 100. For example, in response to a request from a physician, the user interface 126 presents a patient medical history. In other examples, a radiologist is able to retrieve and manage a workload of exams distributed for review to the radiologist by the medical exam distributor 102 via the user interface 126. In further examples, an administrator reviews radiologist workloads, exam allocation, and/or operational statistics associated with the distribution of exams by the medical exam distributor 102 via the user interface 126. In some examples, the administrator adjusts one or more settings or outcomes of the medical exam distributor 102 via the user interface 126.

The example data center 112 of FIG. 1 is an archive to store information such as, for example, images, data, medical reports, and/or, more generally, patient medical records. In addition, the data center 112 can also serve as a central conduit to information located at other sources such as, for example, local archives, hospital information systems/radiology information systems (e.g., the HIS 104 and/or the RIS 106), or medical imaging/storage systems (e.g., the PACS 108 and/or connected imaging modalities). That is, the data center 112 can store links or indicators (e.g., identification numbers, patient names, or record numbers) to information. In the illustrated example, the data center 112 is managed by an application server provider ("ASP") and is located in a centralized location that can be accessed by a plurality of systems and facilities (e.g., hospitals, clinics, doctor's offices, other medical offices, and/or terminals). In some examples, the data center 112 can be spatially distant from the HIS 104, the RIS 106, and/or the PACS 108 (e.g., at General Electric® headquarters).

The example data center 112 of FIG. 1 includes a server 128, a database 130, and a record organizer 132. The server 128 receives, processes, and conveys information to and from the components of the healthcare system 100. The database 130 stores the medical information described herein and provides access thereto. The example record organizer 132 of FIG. 1 manages patient medical histories, for example. The record organizer 132 can also assist in procedure scheduling, for example.

The example medical exam distributor 102 identifies a medical exam needing review and facilitates distribution of the exam to an examiner, such as a radiologist. The medical exam can be stored in the data center 112 or located in any other component of the healthcare system 100. In some examples, the exam distributor 102 can distribute one or more exams to a radiologist using pre-defined load-balancing rules based on one or more characteristics associated with an exam, an examiner, a network of examiners, and/or a healthcare environment.

In some examples, the administrator reviews one or more operational statistics associated with the distribution of the exams by the medical exam distributor 102 across the RIS 106. The administrator can implement one or more adjustments directed to the distribution of the exams by the medical exam distributor 102, based on, for example, the operational statistics. The medical exam distributor 102 dynamically responds to user inputs related to, for example, allocation of exams, acceptance/rejection of exams, assignment of exams, radiologist availability, resource availability, exam characteristics, and/or other user interaction via the user interface 126 to efficiently distribute exams to a reviewing radiologist's workflow in view of administrative review goals. The medical exam distributor 102 further automatically optimizes exam allocation based on the user inputs as well as patterns and trends detected from monitoring of exam distribution and review. In facilitating sharing of exam distribution statuses and/or radiologist characteristics between practitioners and administrators associated with the RIS 106, the medical exam distributor 102 provides for a dynamic workflow management system.

Figure 2:
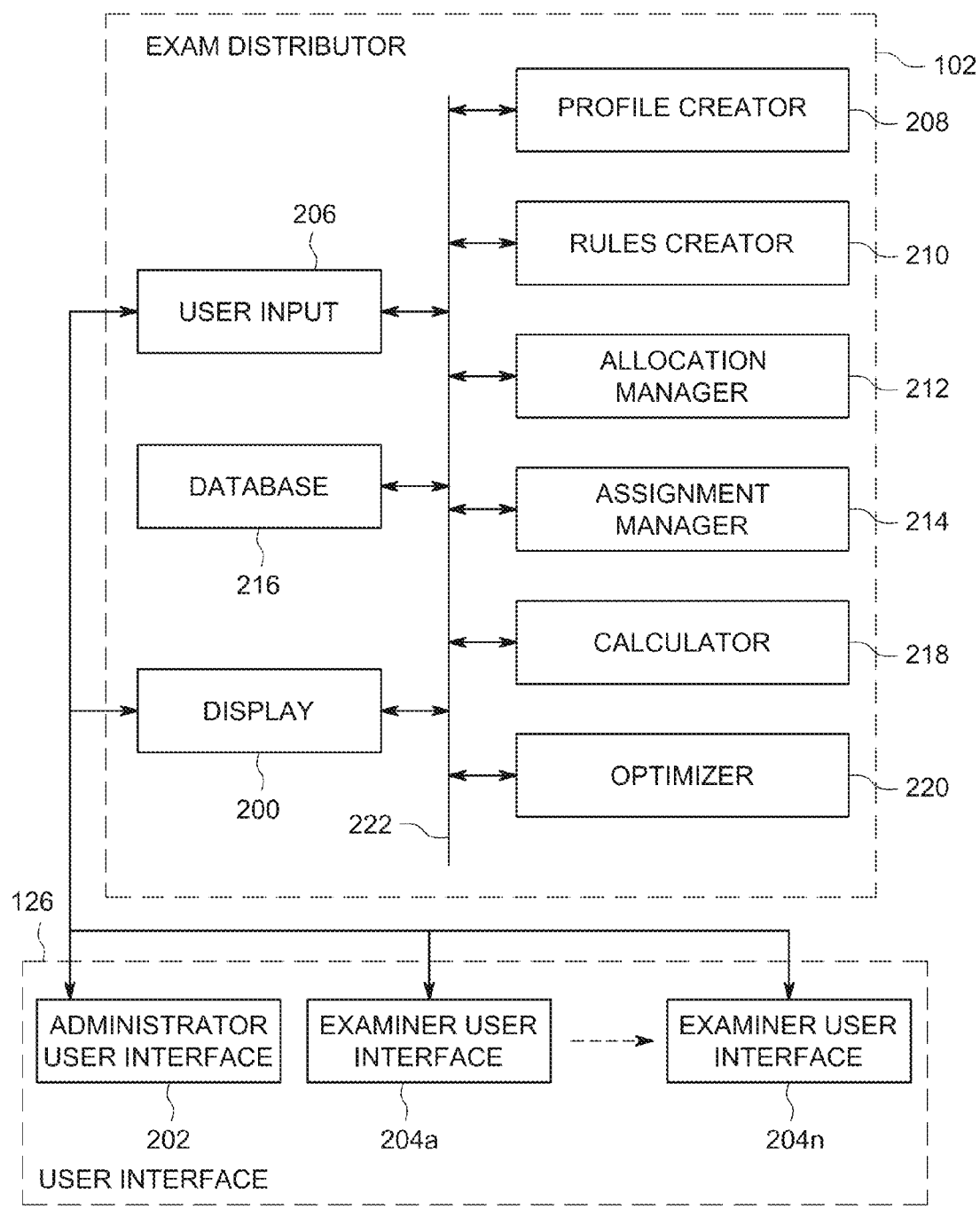
FIG. 2 is a block diagram of the example medical exam distributor of FIG. 1.

FIG. 2 shows a block diagram of the exam distributor 102 of FIG. 1. For example, the exam distributor 102 can be associated with the radiology information system of FIG. 1. The exam distributor 102 includes a display module 200, which interacts, for example, with the user interface 126 of the system 100 of FIG. 1. As will be described below (FIGS. 3-8), in some examples, the user interface 126 is an administrator user interface 202 accessible by, for example, a hospital or radiology department administrator. In further examples, the user interface 126 is an examiner user interface 204a-n accessible by one or more radiologists. The display module 200 can connect to any computer screen, image viewer and/or other display device known to those skilled in the art. The example exam distributor 102 also includes a user input module 206 for receiving, for example, a user input from one or more of the administrator user interface 202 and/or the examiner user interfaces 204a-n.

The example exam distributor 102 also includes a profile creator 208. The profile creator 208 provides for the creation and/or modification of one or more radiologist profiles by a radiologist via the user input module 206. Profiles created via the profile creator 208 can define, for example, a radiologist's specialty, availability, preferred exam attributes, workload capacity, and/or other characteristics associated with the radiologist at select times or on certain days of the week. A radiologist can select a profile via, for example, the examiner user interface 204a, which defines the radiologist's capacity to receive exams for review. In distributing exams for review, the exam distributor 102 at least partially considers the availability and/or workload of a radiologist based on one or more profiles when allocating and/or assigning an exam to the radiologist.

The example exam distributor 102 includes a rules creator 210. The rules creator 210 defines one or more rules used in automatically allocating an exam to a radiologist. In some examples, an administrator can define, for example, one or more departmental and/or institutional rules via the administrator user interface 202 and the user input module 206. Also, in some examples, the rules creator 210 creates rules based on radiologist profiles created by the profile creator 208. In other examples, the rules creator 210 defines one or more load-balancing rules based on, for example, radiologist workload thresholds, radiologist specialties, preferred radiologists, exam priority levels, and/or exam difficulty levels. In implementing the rules creator 210, the example exam distributor 102 optimizes distribution of an exam to a radiologist based a combination of rules associated with a radiologist profile, one or more exam attributes, and/or healthcare administration to match an exam with a reviewing radiologist. Also, in some examples where the exam distributor 102 is implemented across two or more institutions, the rules creator 102 performs a mapping of identifiers associated with the exams and/or the healthcare institutions to standardize exam distribution between institutions. For example, factors such as exam modality, body part, radiologist specialty, and/or institution location are considered by the rules creator as part of defining load-balancing rules. Such mapping across affiliated institutions provides for consistency in applying the load-balancing rules and benchmarks for comparing workload information between radiologists at different institutions.

As shown, the example exam distributor also includes an allocation manager 212. The allocation manager 212 automatically allocates an exam to a radiologist for review. For example, the allocation manager 212 automatically allocates the exam to the radiologist based on one or more rules defined by the rules creator 210. In some examples, the allocation manager 212 automatically allocates an exam to a preferred radiologist based on the radiologist's current workload or workload threshold, specialty, and/or availability. In other examples, the allocation manager 212 automatically allocates the exam to a radiologist based on exam attributes, such as an exam priority level or a service level agreement requiring the exam to be reviewed within a certain amount of time. In further examples, the allocation manager 212 allocates the exam to a radiologist based on one or more combinations of the aforementioned exam and/or radiologist properties.

The example exam distributor 102 also includes an assignment manager 214. The assignment manager 214 assigns an exam to a radiologist. As described above, the allocation manager 212 automatically allocate the exam to the radiologist. However, prior to the allocated exam being reviewed by the radiologist, the radiologist and/or an administrator can review the allocation of the exam to the radiologist via the display 200 (e.g., by interacting with the examiner user interface 204a-n or the administrator user interface 202). Based on, for example, the radiologist's workload, availability, or an exam attribute, the radiologist and/or the administrator can selectively confirm and/or reject the allocation of the exam to the radiologist or decide to redirect the exam to another radiologist for review. The assignment manager 214 facilitates the radiologist's and/or the administrator's decision by confirming assignment and/or acceptance of the exam to the radiologist's workflow.

In other examples, the assignment manager 214 assigns the exam to the radiologist without the allocation manager 212 first allocating the exam to the radiologist. For example, a radiologist, via the user interface 204a-n can direct the assignment manager 214 to assign an unallocated exam to the radiologist's work queue. In other examples, one or more rules defined by the rules creator 210 can bypass the allocation of the exam to the radiologist and cause the assignment manager 214 to automatically assign the exam to the radiologist's workflow without requiring further confirmation.

In other examples, the assignment manager 214 automatically assigns the exam to the radiologist based on radiologist schedules or rules defining preferences for assignment based on exam and/or radiologist attributes. In further examples, the assignment manager 214 automatically delivers exams to the radiologist based on a selection by the radiologist to receive exams for substantially immediate review via the examiner interface 204a-n, rather than delivering exams to the radiologist's work queue for review at a later time. In such examples, the assignment manager 214 can be considered to operate in auto-serve mode such that exams are successively assigned to the radiologist for real-time review.

The example exam distributor 102 also includes a database 216. The database 216 stores information concerning distribution rules, exam allocation information, and/or allocation information. The database 216 also stores information related to one or more radiologists, such as availability and/or profiles. The database 216 also stores information provided to the exam distributor 102 via the user input module 206. Further, the database 216 stores real-time or historical data associated with the distribution and review of exams during operation of the exam distributor 102. For example, during operation of the exam distributor 102, data is generated associated with the exam distribution status, acceptance of exams by radiologists, exam review time, radiologist availability, revenue, etc. Such data can be collected and stored by the database 216. In some examples, the database 216 stores information associated with one or more affiliated institutions in view of exams performed at the individual institutions.

The example exam distributor 102 includes a calculator 218. The calculator 218 generates one or more metrics or statistics based on the data stored in the database 216. Using, for example, data mining techniques, statistical analysis, etc., the calculator 216 generates metrics that provide for real-time and/or historical review of the operation of the exam distributor 102. In some examples, the calculator 216 dynamically updates the metric calculations in response to, for example, user inputs provided via the user input module 205 or adjustments to the allocation manager 212 or the assignment manager 214. In some examples, statistics such as review efficiency and workload are adjusted to account for exams reviewed in auto-serve mode.

The example exam distributor includes an optimizer 220. The optimizer 220 monitors the status of the exam allocation and assignment by the allocation and assignment managers 212, 214 and the metrics calculated by the calculator 218. The optimizer also evaluates user inputs received via the user input module 206 and considers external influences and constraints, such as hospital legal obligations and building resources. As a result of the monitoring, the optimizer 220 detects and analyzes patterns and trends related to the exam distribution. For example, the optimizer 220 detects areas of the workflow allocation process that result in inefficiencies. Further, the optimizer generates improvements to the exam distribution process, including adjustments to one or more rules defined by the rules creator 210. In operation, the optimizer 220 can employ data mining techniques as well as process improvement strategies and tools, including but not limited to, Six Sigma, lean optimization, multivariable testing, capability maturity model integrator (CMMI), behavioral approaches, and/or combinations of global optimization models to drive increase workflow efficiency.

In the example shown, the components of the exam distributor 102, including the display module 200, the user input module 206, the profile creator 208, the rules creator 210, the allocation manager 212, the assignment manager 214, the database 216, the calculator 218, and/or the optimizer 220 are in communication with each other via a communications link 222. The communications link 222 can be any type of wired connection (e.g., a databus, a USB connection, etc.) and/or any type of wireless communication (e.g., radio frequency, infrared, etc.) using any past, present, or future communication protocol (e.g., Bluetooth, USB 2.0, USB 3.0, etc.). Also, the components of the example exam distributor 102 can be integrated in one device or distributed over two or more devices.

While an example manner of implementing the exam distributor 102 of FIG. 1 is illustrated in FIG. 2, one or more of the elements, processes and/or devices illustrated in FIG. 2 can be combined, divided, re-arranged, omitted, eliminated and/or implemented in any other way. Further, the display module 200, the user input module 206, the profile creator 208, the rules creator 210, the allocation manager 212, the assignment manager 214, the database 216, the calculator 218, the optimizer 220 and/or, more generally, the example exam distributor 102 of FIG. 2 can be implemented by hardware, software, firmware and/or any combination of hardware, software and/or firmware. Thus, for example, any of the example display module 200, the user input module 206, the profile creator 208, the rules creator 210, the allocation manager 212, the assignment manager 214, the database 216, the calculator 218, the optimizer 220, and/or, more generally, the example exam distributor 102 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example display module 200, the user input module 206, the profile creator 208, the rules creator 210, the allocation manager 212, the assignment manager 214, the database 216, the calculator 218, the optimizer 220 and/or the exam distributor 102 is/are hereby expressly defined to include a tangible computer readable storage device or storage disk such as a memory, a digital versatile disk (DVD), a compact disk (CD), a Blu-ray disk, etc. storing the software and/or firmware. Further still, the example exam distributor 102 of FIG. 1 can include one or more elements, processes and/or devices in addition to, or instead of, those illustrated in FIG. 2, and/or can include more than one of any or all of the illustrated elements, processes and devices.

FIG. 3 shows the example user interface 126 for interacting with the example exam distributor 102 of FIG. 2. The example user interface 126 can include one or more screens for interacting with the example exam distributor 102, as will be discussed herein in connection with FIG. 3 and FIGS. 4-8 (below).

In particular, FIG. 3 depicts an example first screen 300 of the user interface 126 viewable by an administrator (e.g., the administrator user interface 202 of FIG. 2). The example first screen 300 displays information associated with the distribution of exams by the exam distributor 102. In some examples, the first screen 300 is a dashboard providing an exam status summary of one or more exams requiring review across a radiology department, a hospital, and/or a network of departments or healthcare institutions.

The first screen 300 includes an exam identifier 302. In some examples, the exam identifier 302 is a visual representation of one or more exams requiring review by a radiologist. The exam identifier 302 includes, for example, a name of a patient on which the exam was conducted, an image of the patient, a procedural code, a body part on which the exam was conducted, an exam modality, and/or a time at which the exam was conducted. The exam identifier 302 can also include other, customizable information regarding the exam.

The example first screen 300 also displays one or more exam attribute identifiers 304 that are representative of one or more exam attributes. For example, if a patient is in critical condition and the exam requires urgent review by a practitioner, the exam attribute identifier 304 is highlighted to indicate a priority level associated with the exam. Other exam attribute identifiers 306, 308 can indicate the body part that forms the subject of the exam, whether an exam has been dictated by a practitioner, a name of a prescribing radiologist, a name of radiologist to which the patient has been referred, and/or a relative value unit representative of a difficulty level of the exam. Other exam attributes can be selectively displayed, hidden, and/or removed from the example first screen 300.

The example first screen 300 of the user interface 126 displays one or more exam status identifiers 306, 308, 310. The exam status identifiers 306, 308, 310 are visual indications of the status of the distribution of an exam to a radiologist based on implementation of the exam distributor 102 (including, for example, implementation of the rules defined by the rules creator 210 of FIG. 2). Further, the exam status identifiers 306, 308, 310 dynamically update in response to communicative interactions with the exam distributor 102 via, for example, the user interface 126 (e.g., the administrator user interface 202 and/or the examiner user interface 204a-n). The example first screen 300 also displays an examiner identifier 314 representative of the name of the radiologist to whom the exam has been allocated, assigned, and/or queued.

Figure 4:
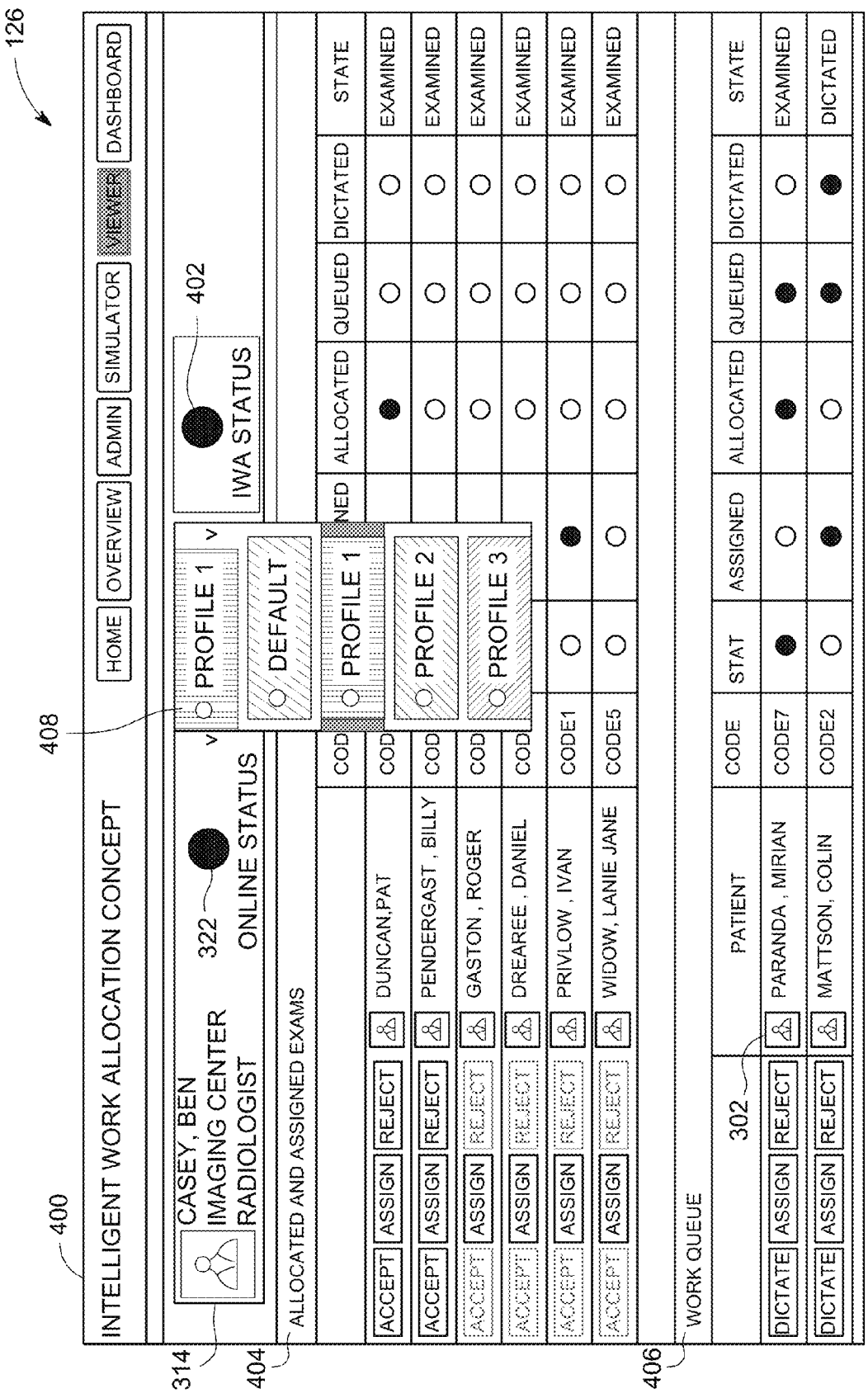
FIG. 4 illustrates an example second screen of an example graphical user interface associated with the example medical exam distributor of FIG. 1.

For example, a first exam status identifier 306 indicates whether an exam has been assigned, via, for example, the assignment manager 214, to a radiologist. A second exam status identifier 308 indicates whether the exam has been allocated to a radiologist, via, for example, the allocation manager 212. A third exam status identifier 310 represents whether, for example, an exam assigned to a radiologist has been accepted for review by the radiologist and moved to the radiologist's work queue (FIG. 4).

The example first screen 300 also displays an alert 316 displayed on the example first screen 300 to indicate whether an exam is reaching a time limit for review. In some examples, an exam is associated with a service level agreement between, for example, a hospital and a health insurance provider, that specifies a time period for review of the exam in order to receive payment. The alert 316 is a visual representative of the expiration of the allocated time for review and whether or not the exam is nearing the expiration time. In some examples, the alert 316 indicates, for example, using via color coding, whether the time allocated for review is past the expiration time, within a threshold of the expiration time, or not yet near the threshold. For example, an unallocated exam associated with the alert 316 representing that the exam is nearing the expiration time can drive an administrator's decision to manually assign the exam to a radiologist so that the exam does not past the expiration time. Also, in some examples, the alert 316 is shared across the administrator and examiner user interfaces 202, 204a-n to provide for monitoring of exam urgency levels across the network and to facilitate a response, if necessary, by the administrator and/or radiologists with respect to prioritizing review of the exams.

As shown in FIG. 3b, the example first screen 300 selectively displays an examiner scorecard 318. In some examples, the scorecard 320 is displayed on a different screen of the user interface 126. The example scorecard 318 includes an examiner summary viewer 320. As shown in FIG. 3b, the examiner summary viewer 320 includes a table containing information about one or more radiologists, including, for example, name, specialty, experience level, seniority, and/or total number of assigned, allocated, and/or accepted exams. A user interacting with the first screen 300 can select to view additional information about a radiologist listed in the examiner summary viewer 318, including, for example, the examiner identifier 314.

An examiner availability indicator 322, which serves as a visual representation of an online status of a radiologist, is also displayed on the example first screen 300. For example, if a radiologist is accessing the radiology information system 106 of FIG. 1, the radiologist is considered to be "available" for purposes of reviewing the allocated exam. The examiner availability indicator 322 can represent a local presence of the radiologist, a remote presence, an offline status, and/or another status associated with an availability of the radiologist. In some examples, the radiologist selectively sets the status of the examiner availability indicator 322 via, for example, the examiner user interface 204a of FIG. 2. Selections by the radiologist are dynamically reflected on the screens of the administrator user interface 202 and the examiner user interfaces 204a-n.

Any of the exam identifier 302; the exam attribute identifiers 304; the exam status identifiers 306, 308, 310; the examiner identifier 314; the alert 316; the scorecard 318; the examiner summary viewer 320; and/or the examiner availability indicator 322 can be dynamically updated based on, for example, implementation of the exam distributor 102 and/or a user's interaction with the user interface 126, including, for example, the administrator user interface 202 or the examiner user interfaces 204a-n. Further, any of the exam or examiner identifiers and/or indicators can be represented on the first screen 300, or any other screen of the user interface 126, using one or more visual representations, including, but not limited to, being flagged/unflagged, highlighted/unhighlighted, displayed/hidden, and/or activated/deactivated. The identifiers and indicators displayed on the example first screen 300 can also be selectively tailored based on, for example, whether the example first screen displays information for a radiology department at a hospital or across a network of healthcare institutions. The order of the display of the identifiers and indicators on the example first screen 300 are not limited to the example illustrations of FIGS. 3 and 3b. Also, the identifiers and indicators of the example first screen 300 can be selectively represented by more or fewer icons. For example, instead of multiple exam status identifiers 306, 308, 310 to indicate the distribution status of an exam, a single exam status identifier can be provided. In some examples, the single exam status identifier can be selectively expanded or collapsed to provide more details about the exam distribution status. In further examples, the exam status identifier(s) and/or the scorecard dynamically update in response to real-time review and reporting of exams by radiologists in auto-serve mode to indicate to the administrator that the exam has been reviewed and to provide a complete assessment of the exam's workload.

In operation, for example, the example first screen 300 of the user interface 126 provides a user, such as an administrator of a radiology network, with an overview of one or more exams requiring review and the workflow distribution status of the exams. For example, the first screen 300 allows the administrator to track the allocation, assignment, and/or acceptance of the exams. The first screen 300 also allows the administrator to track the review status of the exams by displaying, for example, an alert when an exam is reaching a threshold associated with a time allocated for exam review. Additionally, the first screen 300 allows the administrator to selectively view a summary of one or more radiologists' workloads and/or availability status. In some examples, the first screen 300 provides a snapshot of exam distribution status as well as the factors, such as radiologist availability, that influence workflow distribution of exams by the exam distributor 102. Further, in some examples, the administrator considers the information provided on the first screen 300 in managing distribution of exams. Thus, the example first screen 300 serves as a dashboard for an overview of the exam distribution system and a launch pad for further review of workload allocation.

FIG. 4 illustrates an example second screen 400 of the user interface 126 viewable by an administrator (e.g., via the administrator user interface 202 of FIG. 2). The second screen 400 serves as a radiologist workflow summary page by listing exams that the radiologist has been allocated and/or assigned to review by the exam distributor 102. The administrator can view the example screen 400 to review a radiologist's workload. In some examples, the administrator views the second example screen 400 by selecting an examiner identifier 314 associated with a radiologist from the examiner summary viewer 320 of the example first screen 300 (FIG. 3). In other examples, the administrator reaches the example second screen 400 via links provided on one or more other screens of the example user interface 126, or directly upon accessing the user interface 126.

A first portion of the second screen 400 displays identifying information about the radiologist, including, for example, the examiner identifier 314 and/or the examiner availability indicator 322. The second screen 400 also includes a workload availability identifier 402. The workload availability identifier 402 indicates a radiologist's availability to be allocated and/or assigned exams. For example, based on one or more load-balancing rules defined by the rules creator 210, the allocation manager 212 and/or the assignment manager 214 (FIG. 2) can refrain from allocating and/or assigning exams to the radiologist if the radiologist's workload has surpassed a threshold. Accordingly, the workload availability indicator 402 can be deactivated to visually represent that the radiologist is not to be allocated and/or assigned exams. In other examples, the workload availability indicator 402 can be activated to reflect that the examiner is available to receive exams based on a current state of the radiologist's workload. In some examples, the status of the examiner availability indicator 322 is distinct from the workload availability indicator 402. For example, a radiologist can access and/or log into the radiology information system 106 (FIG. 1) and thus, have an online presence, but is unable to be allocated and/or assigned exams because of a workload threshold. Changes to the statuses of the examiner availability indicator 322 and/or the workload availability indicator 402 are dynamically updated across the administrator user interface 202 and the examiner user interfaces 204a-n.

A second portion of the example second screen 400 displays an allocated/assigned exam summary 404. The allocated/assigned exam summary 404 includes a listing of one or more exams that have been allocated to the radiologist by the allocation manager 212 (FIG. 2) and/or assigned to the radiologist by the assignment manager 214 (FIG. 2). In some examples, one or more allocated and/or assigned exams are represented in the allocated/assigned exam summary 404 by the exam identifier 302. In further examples, the allocated/assigned exam summary 404 displays one or more of the exam status identifiers 306, 308, 310 associated the exam.

A third portion of the example second screen 400 of the user interface 126 displays an examiner work queue 406. The examiner work queue 406 contains exams that have, for example, been accepted by and/or assigned to the examiner for review. For example, a radiologist can have an option to accept or reject an exam allocated to the radiologist by the exam distributor 102. Also, as will be discussed below in connection with FIG. 5, the administrator can manually assign an exam to the radiologist. The accepted/assigned exams appear in the examiner work queue 406. An exam can be represented in the examiner work queue 406 by, for example, the exam identifier 302, the exam attribute identifiers 304, and/or one or more of the exam status identifiers 306, 308, 310 associated with the exam. In some examples, the third exam status identifier 310 is flagged to reflect that the exam is in the radiologist's examiner work queue 406.

The second screen 400 also includes a profile selector 408. As described above, the profile creator 208 (FIG. 2) optionally provides for a radiologist to create one or more profiles via, for example, the examiner user interface 204a-n. The one or more profiles can be based on, for example, availability and/or specialty practiced during certain times or on particular days of the week. A profile can affect the distribution of exams to the radiologist by the allocation manager 212 and/or the assignment manager 214. For example, when a radiologist is associated with a certain profile, he/she can be allocated and/or assigned no exams, only a certain number of exams, and/or only exams having certain exam attributes.

The profile selector 408 provides for an administrator to view the radiologist's workload with respect to an available profile created by the radiologist. By selecting a profile on the example second screen 400 (e.g., via a drop down menu), the administrator can view the exams allocated to, assigned to, and/or accepted by the radiologist when the radiologist is associated with the selected profile. Selecting a profile dynamically updates display of, for example, the examiner availability identifier 322 and/or the workload availability identifier 402 based on the parameters of the selected profile.

In operation, the example second screen 400 of the user interface 126 provides for the administrator to view a radiologist-specific workload. For example, the administrator can view exams that have been allocated to the radiologist by the exam distributor 120. The example second screen 400 also enables the administrator to view exams that the radiologist has accepted and, thus, are located in the examiner's work queue. The information provided on the example second screen 400 can be used by the administrator in evaluating the radiologist's current workload in view of, for example, other radiologists. The information displayed via the example second screen 400 can also be used by the administrator in considering whether to assign additional exams to the radiologist, in some examples overriding the allocation by the exam distributor 102 and/or acceptance/ rejection of an exam by the radiologist. Additionally or alternatively, in view of the radiologist-specific information provided on the example second screen 400, the administrator considers adjusting one or more of the load-balancing rules associated with the exam distributor 102.

Figure 5:
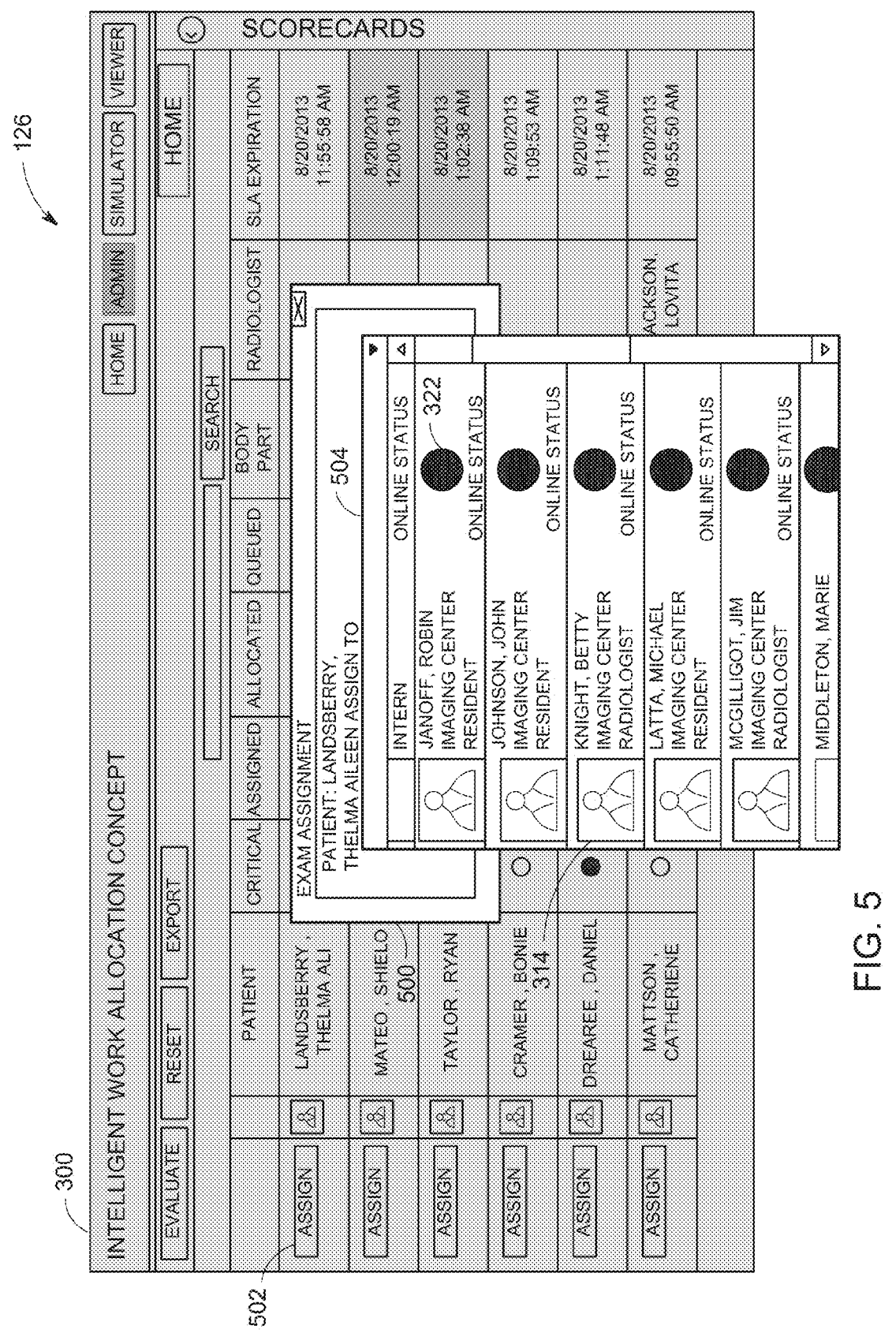

FIG. 5 illustrates an example third screen 500 that can be viewed via the user interface 126, and in particular, the administrator user interface 202. In some examples, the example third screen 500 is accessed by selecting an assignment trigger 502 displayed on the example first screen 300 of FIG. 3. For example, a respective assignment trigger 502 is associated with each exam identifier 302 displayed on the example first screen 300. In other examples, the example third screen 500 is accessed from one or more other screens of the user interface 126.

As described above, the example first screen 300 of FIG. 3 displays information associated with the distribution of exams as well as alerts associated with time limits for reviewing the exams. Also as described above, the example second screen 400 of FIG. 4 displays radiologist-specific workload information. Based on, for example, the exam distribution and review information displayed via the first screen 300 and/or the second screen 400, the administrator can decide to manually assign an exam to a radiologist. The example third screen 500 facilitates such an assignment by serving as an assignment tool.

For example, the administrator can view an exam that has not yet been allocated and/or assigned to a radiologist via the example first screen 300. The administrator can decide to assign the exam to the radiologist based on, for example, the examiner availability indicator 322 associated with a radiologist. To assign the exam, the administrator can select the assignment trigger 502 associated with the exam via the example first screen 300. Selection of the assignment trigger 502 can cause the example third screen 500 to display.

In some examples, the example third screen 500 includes a menu 504 (e.g., a drop-down menu) of radiologists in the network. The menu includes the examiner identifier 314 and the associated examiner availability indicator 322. Other information associated with the radiologists can be displayed via the menu 504. Also, in some examples, one or settings can be configured with respect to the menu 504. For example, the menu 504 can be configured only to display radiologists who are available online, as represented by the respective examiner availability indicator 322. In other examples, the administrator can assign an exam to a radiologist who is offline, as represented by the examiner availability indicator 322.

When the administrator selects to assign an exam to a radiologist via the menu 504, the exam distributor 102 moves the exam to the selected radiologist's examiner work queue 406 (FIG. 4). Also, upon assignment, one or more of the exam status identifiers 306, 308, 310 dynamically updates via the administrator user interface 202 and/or the examiner user interfaces 204a-n to reflect the current status of the exam. In such a manner, the example third screen 500 provides for manual assignment of an exam to a radiologist for review.

In operation, the administrator can decide to assign an exam to a radiologist via the example third screen 500 based on one or more factors associated with the distribution status of exams. For example, activation of the alert 316 indicating that an exam is past due or nearing the expiration time can drive the administrator to manually assign the exam to a first radiologist and/or redistribute the exam to a second radiologist if the exam was previously allocated to the first radiologist. In some examples, upon review of one or more radiologist workloads (e.g., via the assignment/allocation summary provided by the example second screen 400), the administrator decides to redistribute the exams among radiologists. For example, the administrator can assign an exam that was originally allocated by the exam distributor 102 to the first radiologist to the second radiologist if, for example, the second radiologist has a lighter workload than the first radiologist, is available to receive work, or requests assignment of the exam. Other factors or combination of factors related to exam distribution and review can contribute to an administrator's decision to utilize the assignment tool features of the third screen 500.

In other examples, the administrator uses the third screen 500 to override a radiologist's decision to reject allocation of an exam by the exam distributor 102. As described above, in some examples, a radiologist can selectively accept or reject review of an allocated exam. If a radiologist rejects an exam, the exam does not appear in the radiologist's work queue 406. If, upon reviewing the radiologist's workload and/or history with respect to rejecting allocated exams, the administrator decides that the radiologist should review the rejected exam, the administrator can access the example third screen 500 to override the radiologist's rejection of the exam and assign the exam to the radiologist's work queue. In such examples, the radiologist is required to review the assigned exam. The administrator can decide to override the rejection of the exam if, for example, the radiologist has a history of rejecting exams having certain attributes, such as exams associated with a particular body part or modality. The example third screen 500 can be used to prevent such "cherry-picking" of exams by radiologists. Further, the administrator can assign exams to radiologists who are habitually offline to prevent radiologists from avoiding exam assignments overall.

In some examples, the administrator decides to assign an exam to a radiologist via the example third screen 500 based on one or more metrics associated with the operation of the exam distributor 102 and/or, more generally, the radiology information system 106. For example, the administrator is able to view operational statistics and/or performance metrics associated with the distribution and review of exams via the administrator user interface 202. Based on metrics related to, for example, exam review efficiency, the administrator can decide to adjust the allocation and/or assignment of exams among radiologists via the example third screen 500. In other examples, external factors associated with the healthcare environment, such as building and/or equipment resources, can drive the administrator's decision to adjust the exam distribution.

In sum, any combination of the aforementioned factors and/or any other internal and/or external factors can influence the administrator to assign an exam to a radiologist via the example third screen 500. In combination with the example first and second screens 300, 400, the examples third screen 500 provides for the administrator to influence the allocation of exams to selected radiologists in response to monitoring exam and/or radiologist status and in accordance with workflow goals of the radiology network and/or healthcare institution.

Figure 6:
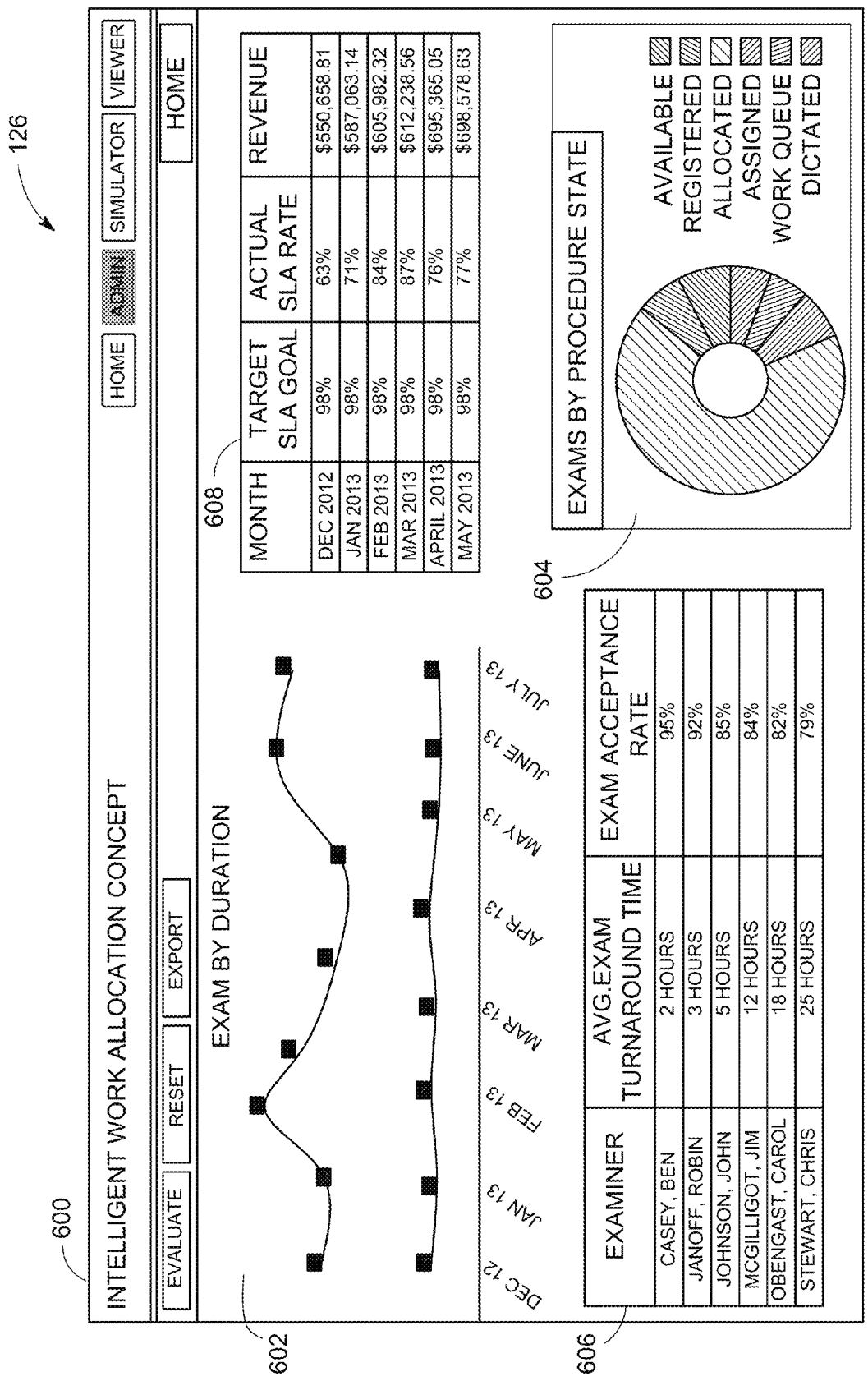
FIG. 6 illustrates an example fourth screen of the example graphical user interface associated with the example medical exam distributor of FIG. 1.

FIG. 6 illustrates an example fourth screen 600 of the example user interface 126 for interacting with the exam distributor 102 of FIG. 2. In particular, the example fourth screen 600 is viewable by an administrator via, for example, the administrator user interface 202 of FIG. 2. As illustrated in FIG. 6, the example fourth screen 600 displays one or more metrics or statistics associated with the current and/or historical operation of the exam distributor 102. The metrics can be presented in dashboard arrangement and include data displayed in graphical format, table format, and/or other formats for organizing and presenting information. In some examples, the metrics displayed on the example fourth screen 400 are calculated for example, by the calculator 218 based on data stored in the database 216 of FIG. 2. In some examples, the metrics are derived from real-time and/or historical data stored in the database 216 using, for example, data mining techniques. In further examples, the metrics displayed on the example fourth screen 400 are dynamically updated during operation of the exam distributor 102.

For example, the fourth screen 600 displays historical metrics associated with distribution and review of exams. As illustrated in FIG. 6, the fourth screen 600 displays an exam tracker 602 (e.g., a graph) that characterizes exams over time based on whether or not review of an exam was completed within the allocated SLA time. Such information allows the administrator to view, for example, exam workloads by month, year, etc. as well as a summary of the performance of the radiologist network in meeting exam review targets over time.

The example fourth screen 600 also displays exam distribution metrics based on real-time data to reflect the current statuses of and characteristics associated with exams requiring review. For example, an exam status summary 604 displays currently pending exams categorized by distribution status. As illustrated FIG. 6, the exam status summary 604 includes a graph visually representing the exams based their status as, for example, allocated, assigned, queued, unassigned, etc. Other approaches for organizing data associated with the pending exams can also be displayed via the example fourth screen 600, including, for example, pending exams organized by type.

In some examples, the example fourth screen 600 displays metrics associated with the radiologists reviewing exams distributed by the exam distributor 102 and/or assigned by, for example, the administrator as described above in connection with the assignment tool of FIG. 5. In some examples, the administrator is interested in viewing examiner-specific performance metrics including, but not limited to, average turnaround time for reviewing exams, acceptance rate of exams automatically allocated to the radiologist by the exam distributor 102, examiner efficiency, and/or number of days the examiner was available/unavailable over a period of time. Such radiologist-level statistics, displayed via, for example, an examiner performance tracker 606 (e.g., a table), can be used by the administrator to evaluate a radiologist's performance over time and/or in view of other radiologists. Statistics contained in the example examiner performance tracker 606 can also be used by the administrator in assessing the automatic allocation of exams to radiologists by the exam distributor 102. For example, a review of examiner turnaround times as displayed in the examiner performance tracker 606 can drive the administrator to consider adjusting one or more of the rules and/or parameters of the exam distributor 102, as will be described below in connection with FIG. 7. In other examples, the administrator decides to manually adjust the distribution of exams based on the examiner performance tracker 606 via, for example, the example third screen 500 of FIG. 5.

In some examples, the example fourth screen 600 further displays metrics associated with administrative goals, constraints, obligations, and/or other factors that are associated with the distribution and review of exams at an institutional level. In some examples, as described above, a healthcare facility has a contractual service level agreement (SLA) with a health insurance provider that associates time allocated for exam review with payment. In some examples, the example fourth screen 600 includes an institutional metric reviewer 608 (e.g., a table) containing data about SLA goals and/or rates over time with associated revenue information. In such examples, the fourth screen 600 serves as a dashboard for the administrator to view statistics associated with exam review performance that can influence healthcare administration, financial considerations, and/or clinical strategies across the network, healthcare facility, and/or group of healthcare facilitates.

The display of information via the example fourth screen 400 is not limited to the exam tracker 602, the exam status summary 604, the examiner performance tracker 606, and/or the institutional metric reviewer 608. Rather, the example fourth screen 400 can display more or less metrics or display the metrics in a different arrangement than illustrated by FIG. 6. In some examples, the administrator selects one or more metrics to display on the example fourth screen 600 by adjusting one or more settings via the user interface 126.

The example fourth screen 600 of FIG. 6 serves as dashboard for the administrator to view one or more operational statistics associated with the distribution of exams across the radiology network and/or healthcare institution. The metrics presented via the fourth screen 600 can be derived using data mining and analytics techniques to facilitate review, and in some examples, action by the administrator with respect to the distribution of exams. For example, in reviewing a radiologist's performance via the examiner performance tracker 606, the administrator may wish to adjust the distribution of exams to the radiologist. In such examples, the administrator may prefer to make discrete or one-time adjustment to the distribution of exams. As described above, the example first and third screens 300, 500 of FIGS. 3 and 5 facilitate a manual adjustment to exam allocation or assignment (e.g., via the assignment trigger 502 and the menu 504).

In other examples, monitoring of the historical exam data via the exam tracker 602 and/or the institutional metric reviewer 608 can result in the administrator deciding to adjust the distribution of exams across the radiology network based on patterns, trends, and/or observations reflected in the data. In some examples, the administrator may wish to implement or suggest an adjustment to the exam distributor 102 that institutes new exam distribution criteria, prompts a permanent or semi-permanent change to a distribution parameter, or has other effects beyond, for example, a discrete adjustment. To facilitate such a network-wide adjustment, the administrator may wish to revise one or more of the load-balancing rules that drives the allocation of exams.

Figure 7:
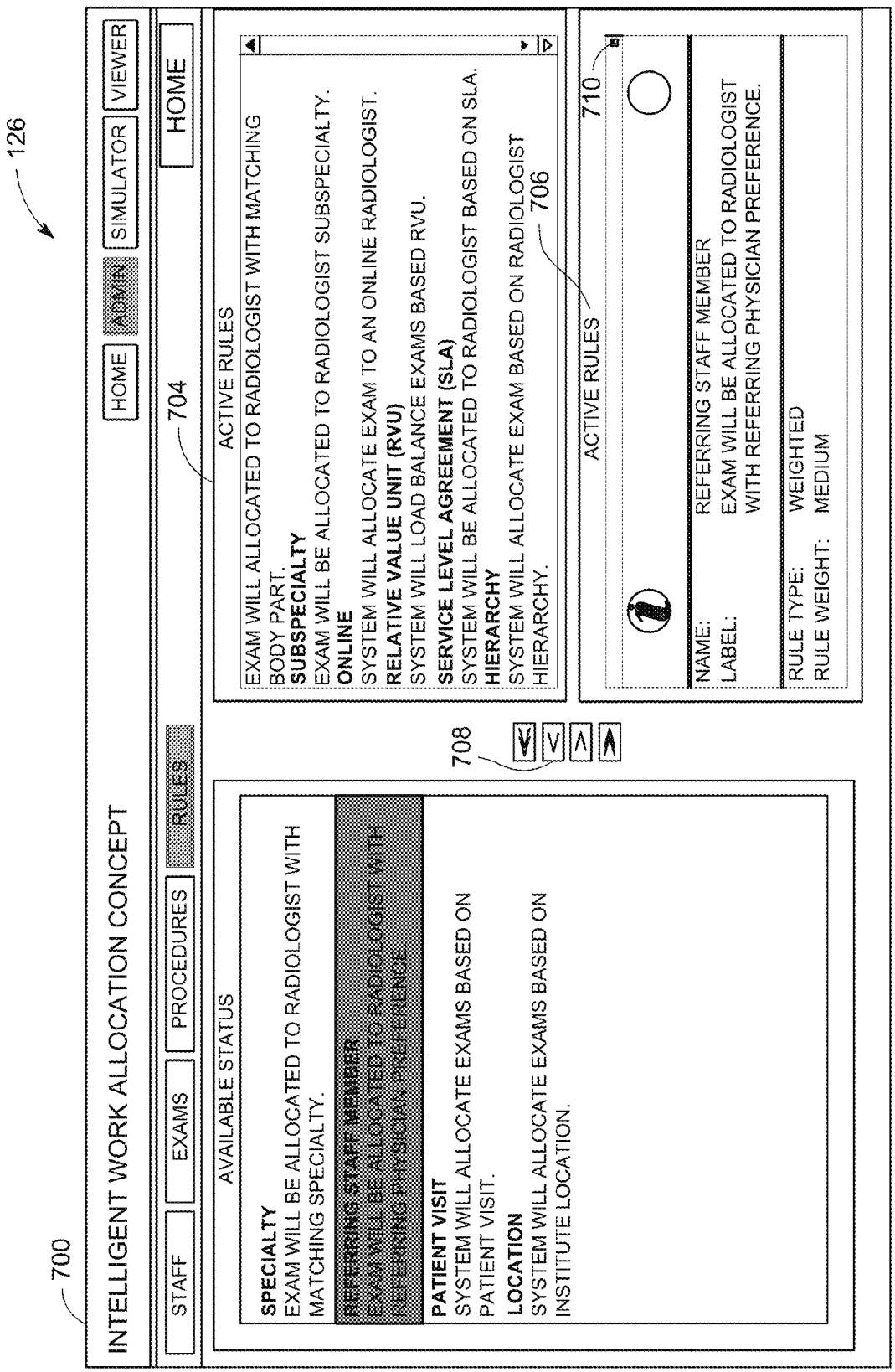
FIG. 7 illustrates an example fifth screen of the example graphical user interface associated with the example medical exam distributor of FIG. 1.

To implement a rule-based adjustment, the user interface 126 provides for the administrator to review, and in some examples, edit the rules. FIG. 7 illustrates example fifth screen 700 of the example user interface 126 for interacting with the exam distributor 102 of FIG. 2. In particular, the example fifth screen 700 is viewable by an administrator via, for example, the administrator user interface 202 to review and/or facilitate adjustments to the one or more rules created by the rules creator 210 of the exam distributor 102 of FIG. 2.

The example fifth screen 700 serves as a rules viewer, in that the fifth screen 700 provides an overview of the load-balancing rules created by the rules creator 210. For example, the fifth screen 700 includes an available rules summary 702 (e.g., a listing). The available rules summary 702 displays rules that are available for implementation by the exam distributor 102, but are not currently be used by the exam distributor 102 in allocating exams. The fifth screen 700 also includes an active rules summary 704 (e.g., a listing) that displays rules that are currently being implemented by the exam distributor 102 in the automatic allocation and/or assignment of exams to radiologists. In some examples, factors such as exam characteristics, radiologist characteristics, or institutional resources determine whether a rule is available or actively being implemented by the exam distributor 102. In some examples, whether a rule is characterized available or active is dynamically updated based on changes in the aforementioned factors and/or other internal or external considerations during operation of the exam distributor 102.

The example fifth screen 700 also includes a rule detail summary 706. By selecting, for example, a rule from the available rules summary 702 and/or the active rule summary 704, the rule detail summary 706 displays details about the selected rule, including, but not limited to, criteria such as the rule name, a rule description, whether the rule has any weight in affecting the distribution of exams, and the degree of weight given to the rule.

In viewing the available and/or active rules, the administrator may wish to adjust the rules implemented by the exam distributor 102. Using, for example, a rules controller 708, the administrator can selectively designate that an available rule listed in the available rules summary 702 should be actively implemented by moving the selected available rule to the active rules summary 704. As a result, the exam distributor 102 automatically implements the newly designated active rule when distributing exams. Additionally or alternatively, the administrator can selectively remove an active rule from being implemented by the exam distributor 102 using the rules controller 708. For example, by moving a selected rule from the active rules summary 704 to the available rules summary 702, the exam distributor 102 no longer implements the deactivated rule when allocating exams. In such a manner, the rules controller 708 provides for the administrator to selectively control the implementation of rules by the exam distributor 102. For example, based on one or more metrics viewed via the example fourth screen 600 (FIG. 6), the administrator can decide to active or deactivate one or more rules via the example fifth screen 700.

Additionally or alternatively, the example fifth screen 700 provides for editing of one or more of the available rules or the active rules. As described above, upon selecting a rule from the available or active rules summaries 702, 704, the rules detail summary 706 displays details about the selected rule. Using, for example, a rules editor 710, the administrator can revise, update, add, delete, or, more generally, change the characteristics associated with the rule. In some examples, the administrator makes changes to, for example, the weight given to the rule by the exam distributor 102, based on one or more metrics viewed via the example fourth screen 600 (FIG. 6). Also, in some examples of the fifth screen 700, the administrator has an option to create a new rule and/or delete an existing rule. In response to changes to the details associated with the rules via the rules editor 710, the exam distributor 102 automatically implements the rules in accordance with the adjustments when allocating exams.

In operation, the example fifth screen 700 serves as a rules viewer that allows the administrator to view the available and active rules associated with the distribution of exams by the exam distributor 102. Upon viewing current and/or historical operational metrics associated with the distribution and review of exams, the administrator can decide to review the rules via the example fifth screen 700. Further, in some examples, the administrator may wish to revise one or more of the details associated with a rule and/or selectively deactivate or activate a rule from implementation by the exam distributor 102. In adjusting the rules via the example screen 700, the administrator can influence the workflow allocation across the radiology network, as the exam distributor 102 applies the rules in allocating exams for associated radiologists. Thus, in interacting with the rules viewer of the example screen 700, the administrator can selectively influence rule implementation and outcomes to facilitate improvements to exam workflow allocation across the network.

Figure 8:
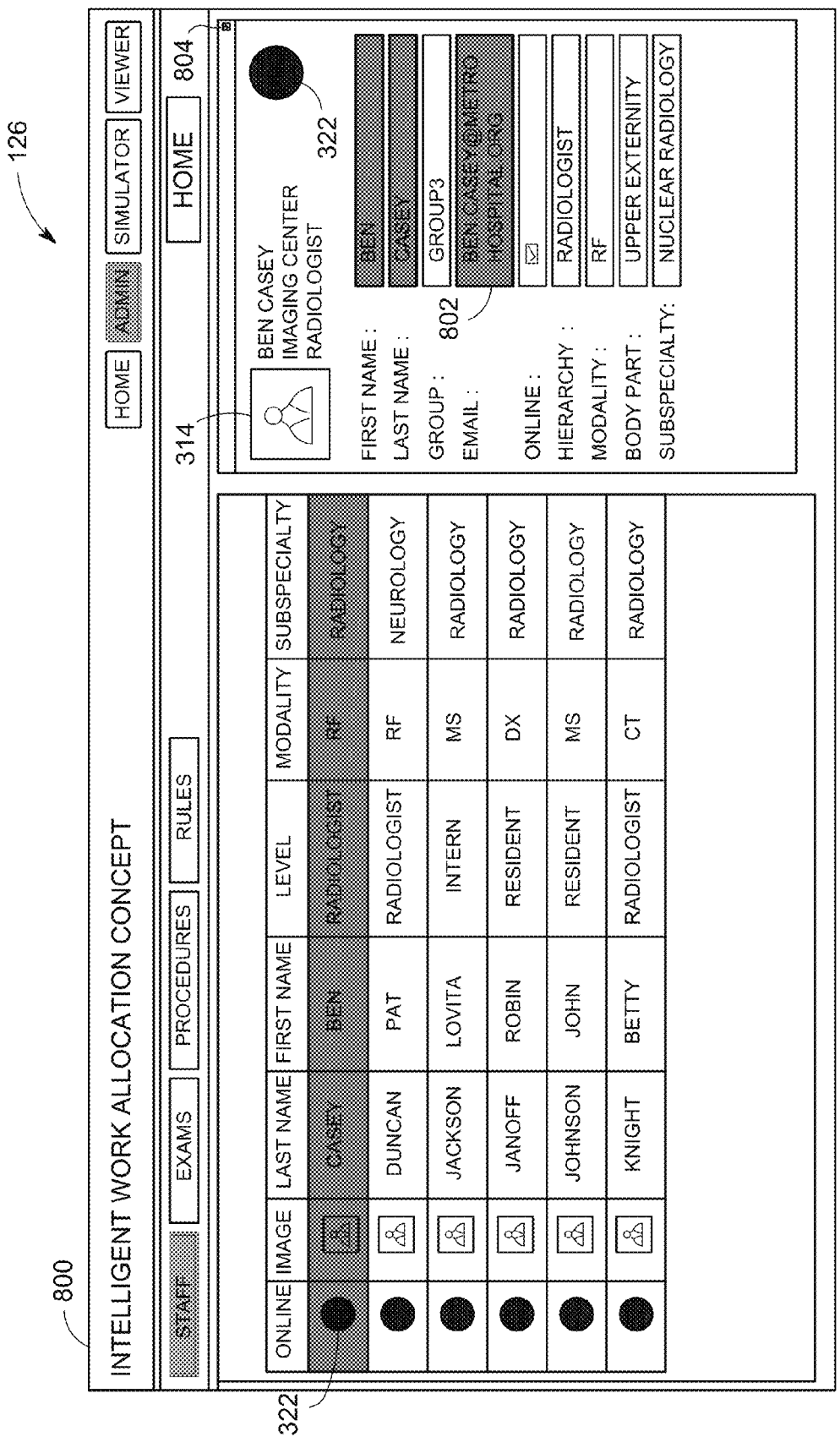
FIG. 8 illustrates an example sixth screen of the example graphical user interface associated with the example medical exam distributor of FIG. 1.

In some examples, the user interface 126 enables the administrator to review and update radiologist attributes that are referenced by the exam distributor 102 in implementing the load-balancing rules. FIG. 8 illustrates an example sixth screen 800 of the example user interface 126 for interacting with the exam distributor 102 of FIG. 2. In particular, the sixth screen 800 is viewable by an administrator via, for example, the administrator user interface 202 to review, and, in some examples, update attributes associated with the radiologists of the network.

As shown in FIG. 8, the example sixth screen 800 displays the examiner identifier 314 and the examiner availability indicator 322. The example sixth screen 800 can display other radiologist attributes 802, including, but not limited to, specialty, institution, experience level, contact information, etc. In some examples, the administrator updates one or more of the radiologist attributes 802 via a radiologist attribute editor 804. For example, by selecting the examiner identifier 314 associated with a radiologist, the administrator can revise the radiologist's sub-specialty in view of the radiologist's qualifications via the radiologist attribute editor

804. Changes to the radiologist attributes via the example sixth screen 800 are dynamically considered by the exam distributor 102 in automatically allocating exams to the radiologists.

The example sixth screen 800 operates in association with the rules viewer of the example fifth screen 700 of FIG. 7, and more generally, the examples first through fifth screens of FIGS. 3-7, to provide the administrator with tools to influence the workflow allocation outcomes by reviewing, editing, updating, adjusting, and/or overriding the distribution of exams to radiologists. Other screens can additionally or alternatively be provided to the administrator with respect to exam distribution. For example, screens displaying procedural code information, institutional information, and/or calendar views of radiologist availability profiles can be viewed via the example user interface 126, and more particularly, the administrator user interface 202. In some examples, a user configures the screens and/or the information displayed on the screens of the user interface 126.

Figure 9:
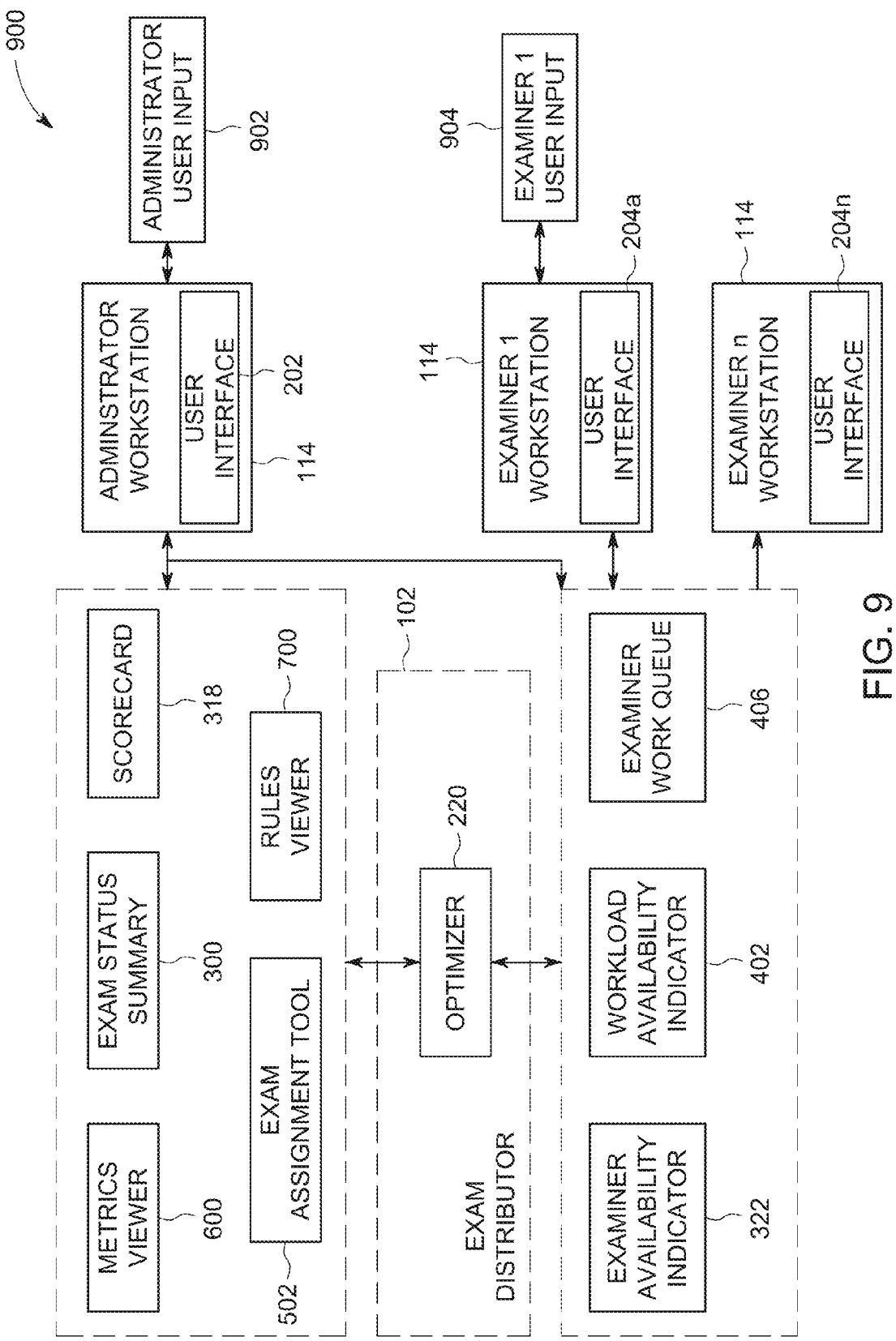
FIG. 9 depicts an interactive relationship between the example medical distributor of FIG. 1 and the example screens of FIGS. 3-8.

As described above, the example user interface 126 enables the administrator to monitor the distribution and review status of exams requiring review and in some examples, to influence the outcomes of the workload allocation by instituting radiologist-specific and/or network-level adjustments (e.g., via screens 300-800 of FIGS. 3-8). Whereas in some examples the administrator has an option to make adjustments based on operational statistics to increase the efficiency of exam review, the exam distributor 102 also includes an inherent monitoring and improvement feature to automatically review the exam distribution data, consider user inputs, detect patterns and trends observable from the data, and optimizes the parameters of the load-balancing rules that drive the distribution of the exams. In FIG. 9, such an automated review is performed by the example optimizer 220 of the exam distributor 102 of FIG. 2.

For example, FIG. 9 depicts an example interactive relationship 900 between the optimizer 220 of FIG. 2, the screens 300-800 of FIGS. 3-8 of user interface 126, and user inputs received via one or more administrator and/or examiner workstations 114. For example, the administrator can access the administrator user interface 202 at the respective workstation 114 and view, for example, the examiner scorecard 318, the exam distribution status summary associated with the example first screen 300, the metrics viewer associated with the example fourth screen 600, and/or the rules viewer associated with the example fifth screen 700. The administrator can also provide one or more administrator user inputs 902 via the administrator user interface 202. For example, as described above, the administrator can provide a user input 902 to the exam assignment tool 502 to direct assignment of an exam to a radiologist.

The administrator can also view the examiner availability indicator 322, the workload availability indicator 402, and/or the examiner work queue 406 as part of the administrator's ability to review radiologist and exam workflow characteristics via the administrator user interface 202. Such indicators and identifiers are also viewable by the radiologist via the examiner user interfaces 204*a-n* via the workstations 114. For example, a first radiologist can provide an examiner user input 904 via the examiner user interface 204 to update the examiner availability indicator 322 (e.g., to indicate an online or offline presence). The status of the examiner availability indicator 322 is dynamically updated and viewable to the administrator via the administrator user interface 202 as well as to one or more radiologists n via the examiner user interface 204*n*

During allocation of the exams by the exam distributor 102 (e.g., by the allocation and assignment managers 212, 214) and as the administrator and/or the radiologists interact with the user interfaces 202, 204*a-n*, the optimizer 220 of the exam distributor 102 continuously monitors the exam distribution, the data generated in connection with the exam distribution, and the user inputs to determine workflow efficiency. For example, as exams are allocated to radiologists based on load-balancing rules (e.g., via the allocation manager 212 of FIG. 2), the optimizer 220 monitors the examiner work queues 406, changes in examiner and/or workload availability indicators 322, 402, and the scorecard 318. The optimizer also detects user inputs received via the administrator and examiner user interfaces 202, 204*a-n*. For example, the optimizer detects if an exam was redirected from a first radiologist to a second radiologist via the exam assignment tool 502. The optimizer also detects administrator-initiated changes to the one or more rules via the rules viewer of the example fifth screen 700.

The optimizer 220 also monitors the statistics and metrics generated during the operation of the exam distributor 102. For example, the optimizer 220 tracks real-time data associated with the distribution of exams, such as exam review turnaround times, radiologist workloads, and exam type. The optimizer 220 further considers the real-time data in view of historical workflow data previously collected, such as radiologist availability, exam review efficiency, and revenues. Additionally, the optimizer 220 considers inherent attributes or constraints associated with the distribution of exams, including, but not limited to, exam difficulty levels, contractual obligations, building resources, and clinical practice standards. The optimizer 220 can consider other factors or statistics related to the exams and radiologists. For example, in some instances, the exam distributor 102 provides for exams to be auto-served to radiologists for real-time review of exams, such that the exams are not allocated to the radiologist's work queue, but instead delivered to the radiologist and substantially immediately reviewed upon distribution by the radiologist via the examiner interface 204*a-n*. In such examples, the optimizer 220 considers the efficiency of the radiologists in reviewing exams that have been auto-served and the effects of the auto-served exams on radiologist workloads.

In light of the aforementioned metrics and characteristics, the optimizer 220 detects patterns or trends from the real-time and historical data as well as from the user interactions via the user interfaces 202, 204*a-n*. The optimizer 220 measures and analyzes the efficiency of the exam distribution and review process and determines areas for improvement in the workflow to increase efficiency and/or remove inefficiencies. For example, in view of metrics associated with exam turnaround times, the optimizer 220 can detect an imbalance in exam distribution in light of available resources and radiologists. The optimizer considers instances of exam turnaround times that were above certain thresholds (e.g., exams reviewed prior to expiration of the allocated time for review) as well as below certain thresholds (e.g., exams that expired with respect to the allocated review time). Based on an analytic review of the exam distribution process, the optimizer 220 develops one or more adjustments to the load-balancing rules directed toward improving the efficiency of the exam workflow. In some examples, the optimizer 220 analyzes workflow efficiency and develops process improvements using one or more global optimization models, including, but not limited to Six Sigma, lean optimization, multivariable testing, and/or behavioral approaches.

In some examples, as part of developing a process improvement, the optimizer 220 considers an impact of the adjustment on the remainder of workflow. For example, with respect to a workflow change affecting radiologists associated with a particular specialty, the optimizer 220 also considers the impact of the workflows for radiologists not associated with the particular specialty. In examples where the exam distributor 102 is implemented across one or more institutions, the optimizer evaluates the impact of the proposed changes across the institutions.

In some examples, the optimizer automatically feeds the process improvement to, for example, the rules creator 210, the allocation manager 212, the assignment manager 214 (FIG. 2) for implementation during the operation of the exam distributor 102. In other examples, prior to implementing an adjustment to the load-balancing rules, the optimizer 220 presents the proposed change to the administrator for approval via the administrator user interface 202 (e.g., via the rules viewer of the example fifth screen 700). In such examples, the administrator can approve or reject the proposed change. Upon implementation of the optimization or the process improvement, any resulting changes to the workflow are dynamically reflected throughout the exam distributor 102 and the components of the administrator and examiner user interfaces 202, 204a-n. Thus, as illustrated in FIG. 9, the optimizer considers data and feedback associated with the distribution of exams, and also provides for process improvements impact workflow management.

In some examples, the monitoring and analysis performed by the optimizer 220 is continuous during operation of the exam distributor 102. In other examples, the optimizer 102 performs data analysis and efficiency review as part of a review cycle at specified intervals. Additionally or alternatively, in some examples, the administrator can facilitate the optimization analysis by the optimizer 220 by directing the exam distributor 102 to perform an analysis in view of metrics generated by the calculator 218. For example, the metrics viewer of the example fourth screen 600 and/or the rules viewer of the example fifth screen 700 enable the administrator to initiate the optimization process.

In operation, the optimizer 220 operates as part of an interactive relationship with the components of the exam distributor 102 and the administrator and examiner user interfaces 202, 204a-n to optimize allocation of the exams with the goal of improving workflow efficiency. The optimizer 220 continuously monitors the status of the exam distribution and review and detects patterns with respect to workflow efficiencies and inefficiencies. Based on the monitoring, the optimizer 220 develops process improvements directed toward increasing the efficiency of the exam distribution workflow. The optimizer 220 complements the review of operational statistics by the administrator in that the optimizer 220 performs ongoing data analysis to identify inefficiencies that, in some cases, are not be readily apparent to the administrator, based on current and historical trends in exam distribution. The optimizer generates process improvements in view of detected inefficiencies and in consideration of the impact of the improvements throughout the exam distribution system. In addition, the optimizer considers external factors such as hospital legal obligations when developing process improvements. The optimizer 220 can automatically implement improvements to the exam allocation process or can present the proposed adjustments to the administrator for further administrative review. Thus, the optimizer 220 serves to increase exam allocation efficiency.

The optimizer 220 detects patterns with respect to the receipt and review of exams by radiologists in the network to educate administrators and radiologists as to opportunities for improvement in workflow management. For example, the exam distributor 102 distributes exams to radiologists, including a first radiologist and a second radiologist, based on availability of the first and second radiologists, expiration of the allocated review time for the exams, and degrees of exam difficulty. In some examples, the first radiologist is available to review exams in the mornings during the week and the second radiologist is available only two days a week, but for the entire day. The optimizer 220 detects patterns in the exam-reviewing behavior of the first radiologist and the second radiologist during their available times. For example, the optimizer 220 references exam turnaround times and efficiency metrics associated with the first radiologist and the second radiologist (e.g., metrics generated by the calculator 218). In some examples, the optimizer 220 detects that the first radiologist receives fewer exams from the allocation manager 212 than the second radiologist, but the first radiologist consistently reviews the allocated exams before the expiration of the allocated review time. The optimizer 220 also detects that the second radiologist is distributed more exams than the first radiologist, receives exams with a higher difficulty level, and has a longer exam turnaround time than the first radiologist.

In response to such examples observations, the optimizer 220 dynamically adjusts the load-balancing rules that drive the distribution of exams to the first radiologist and the second radiologist. In some examples, in view of the shorter exam turnaround time associated with the first radiologist, the optimizer 220 adjusts the rules so that the first radiologist receives an increased number of exams associated with lower degrees of exam difficulty during his availability periods. Additionally, the optimizer 220 adjusts the rules so that the second radiologist receives fewer exams on his available days, but the exams have increased difficulty levels. Thus, the optimizer 220 seeks to capitalize on the first radiologist's efficiency rates by providing first radiologist with more exams that can be reviewed within short periods of times. The optimizer 220 also directs the exam distributor 102 to distribute fewer exams to second radiologist, but which have higher degrees of difficulty in accordance with the all-day availability periods of the second radiologist. In light of the workflow adjustments by the optimizer 220, administrators, as well as the first and second radiologists can identify opportunities, for example, for the first radiologist to be regularly referred to for exams requiring minimal review times or for the second radiologist to develop a practice in reviewing exams associated with certain attributes requiring longer periods of review.

Figure 10:
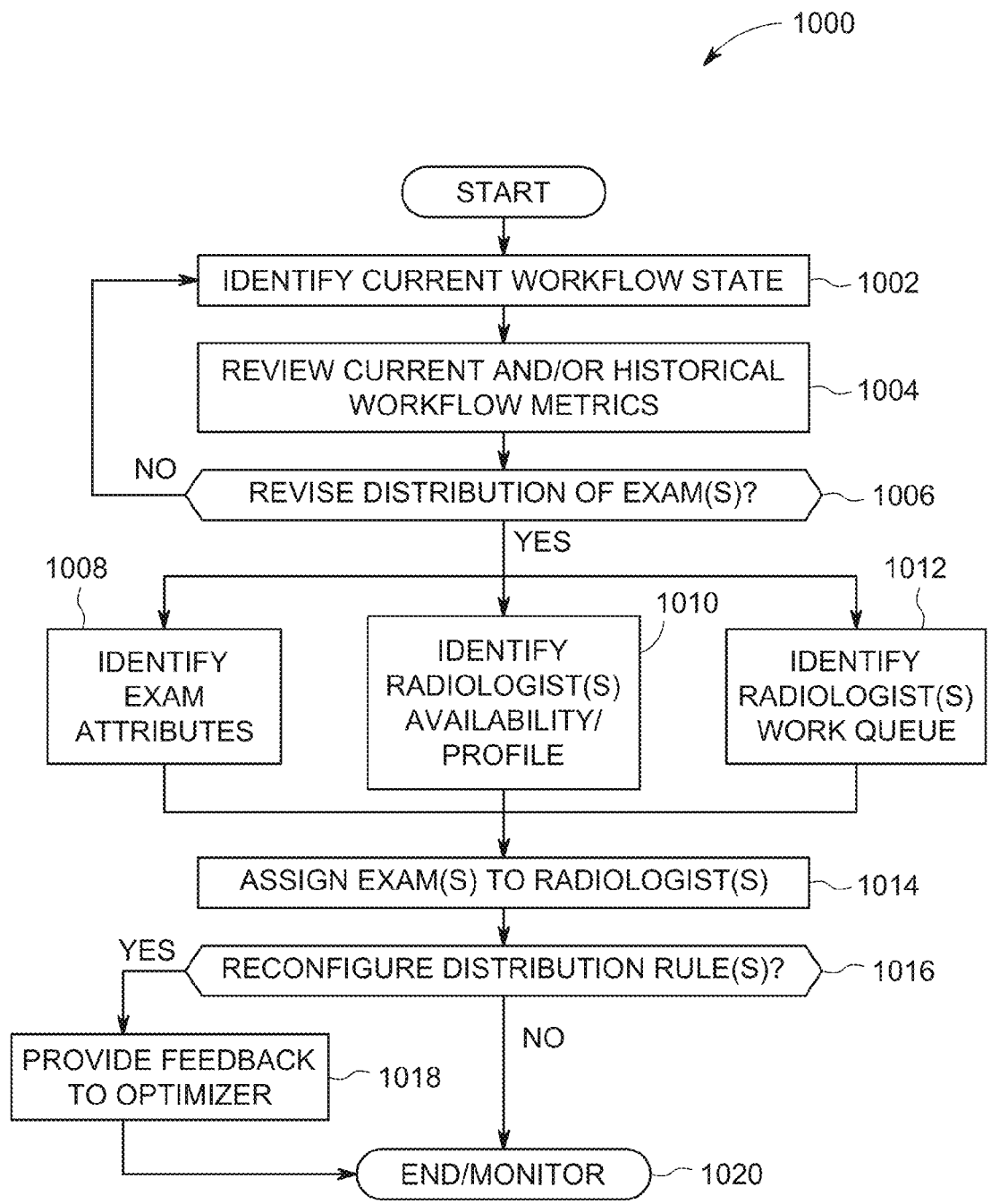
FIG. 10 is a flow diagram illustrating an example method for managing exam distribution via an example graphical user interface associated with the example medical exam distributor of FIG. 1.
Figure 11:
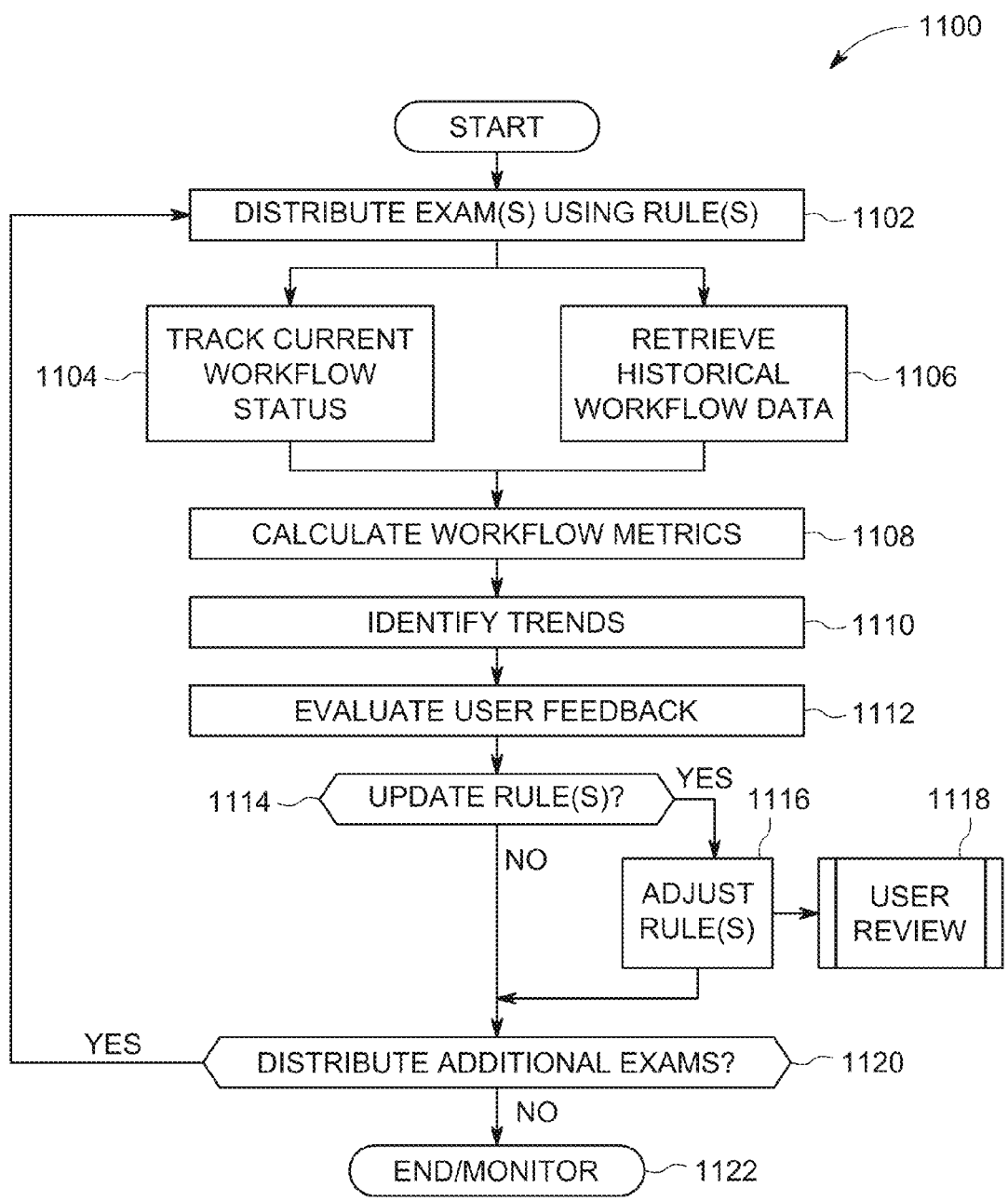
FIG. 11 is a flow diagram illustrating an example method for optimizing exam distribution by the example medical exam distributor of FIG. 1.

Flowcharts representative of example machine readable instructions for implementing the example exam distributor 102 of FIG. 1 are shown in FIGS. 10 and 11. In these examples, the machine readable instructions comprise a program for execution by a processor such as the processor 1212 shown in the example processor platform 1200 discussed below in connection with FIG. 12. The program can be embodied in software stored on a tangible computer readable storage medium such as a CD-ROM, a floppy disk, a hard drive, a digital versatile disk (DVD), a Blu-ray disk, or a memory associated with the processor 1212, but the entire program and/or parts thereof could alternatively be executed by a device other than the processor 1212 and/or embodied in firmware or dedicated hardware. Further, although the example program is described with reference to the flowchart illustrated in FIGS. 10 and 11, many other methods of implementing the example exam distributor 102 can alternatively be used. For example, the order of execution of the blocks can be changed, and/or some of the blocks described can be changed, eliminated, or combined.

As mentioned above, the example processes of FIGS. 10 and 11 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 10 and 11 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 10 illustrates a flow diagram of an example method 1000 to manage medical exam distribution. The example method 1000 implements the exam distributor 102 of FIG. 2. In particular, the example method 1000 includes a method for managing distribution of a medical exam to a radiologist via the administrator user interface 202 of FIG. 2 (e.g., via the example screens 300-800 of FIGS. 3-8). In some examples, the example method 1000 can be performed manually by an administrator. In other examples, the example method 1000 can be implemented via one or more rules defined by, for example, the administrator via the rules creator 210 (FIG. 2).

The example method 1000 begins at block 1002 with identifying the current workflow state of the exams requiring review by radiologists. In some examples, the pending exams are automatically allocated to radiologists by the allocation manager 212 based on one or more rules defined by the rules creator 210 of FIG. 2. In some examples, the exams are allocated based on, for example, a radiologist's schedule, a request by a referring physician to have a specific radiologist review the exam, and/or other user inputs. The allocated exam can be represented on a screen, such as the exam status summary screen of the example first screen 300 of FIG. 3 by an exam identifier 302. The workflow states of the exams can be represented on the example first screen 300 by one more exam status identifiers 306, 308, 310, as being allocated, assigned, queued, etc.

At block 1004, the example method 1000 includes reviewing current and/or historical workflow metrics associated with the distribution of exams. For example, the administrator can view one or more metrics associated with the exam distribution via the example fourth screen 600, including, but not limited to, exam review efficiency, exams categorized by type, revenues, and examiner availability history. Also, the administrator can view a grouping of examiners by workload and experience via the examiner scorecard 318.

Based on the identification of the current workflow state (block 1002) and the review of the current and/or historical workflow metrics (block 1004), the administrator may decide to revise the distribution of one or more of the currently pending exams. At block 1006, a decision is made whether to redistribute one or more the exams. If, for example, the administrator does not wish to revise the exam distribution, the example method 1000 returns to block 1002 for continued monitoring of the exam distribution process by the exam distributor 1002.

If the administrator decides to revise the distribution of exams, the example method 1000 facilitates adjustments to the allocation and/or assignment of exams to the radiologists. In considering how to redistribute an exam, the administrator can consider various attributes associated with the exam and the examining radiologists. For example, at block 1008, the administrator identifies the exam attributes, including, but not limited to, exam modality, body part under review, difficulty level, and expiration time (e.g., the exam attributes 304,316 of FIG. 3). At block 1010, the administrator identifies attributes associated with the radiologists in the network. For example, the administrator identifies the examiner availability indicator 322 (FIG. 3) and the workload availability indicator 402 (FIG. 4) of the radiologists to identify radiologists who are available to receive the exam. The administrator can also consider other radiologist attributes, including, for example, radiologist availability profiles, experience level, and specialty. At block 1012, the administrator reviews the radiologist work queues (e.g., the work queues 406 of FIG. 4) to identify current radiologist workloads.

At block 1014, the example method 1000 includes assigning the exam to a radiologist identified based on the review of exam and radiologist attributes conducted at blocks 1008-1010. For example, in view of exam specialty and the amount of allocated time remaining for review of the exam, the administrator can assign the exam to radiologist who is currently available, capable of being assigned work, shares the specialty, and/or has a lighter work queue than the radiologist to whom the exam was originally assigned. Assignment of the exam at block 1014 is facilitated via the exam assignment tool of the example third screen 500 (e.g., the assignment trigger 502, the menu 504 of FIG. 5). Upon assignment, the exam appears in the examiner work queue 406 for the newly selected radiologist. Also, in some examples, the administrator has reviewed the characteristics associated with the allocated exam and/or the first radiologist of blocks 1008-1010, but decides to assign the exam to the first radiologist in spite of one or more of the characteristics. For example, the administrator can assign the exam to the first radiologist even if the first radiologist is not currently available (e.g., is offline).

In some examples, the administrator revises distribution of one or more exams in view of, for example, an isolated or infrequent reason. For example, a sudden, but non-permanent change in a radiologist's availability or a particularly heavy influx of examples that is only expected to be temporary drives the administrator's decision to manually reallocate the exam. In other examples, the administrator prefers to implement the revised exam distribution on a semi-permanent or permanent basis, on a network-wide level, or as part of a suggested improvement to the exam distribution process.

At block 1016, a decision is made whether to reconfigure the load balancing rules that drive the distribution of the exams. As described above, in some examples, the administrator revises the distribution as part of a discrete event. In such examples, the example method 1000 ends at block 1020, with the administrator continuing to monitor the workflow distribution.

If a decision is made at block 1016 to reconfigure the rules, the example method 1000 includes providing feedback to the optimizer of the exam distributor 102 (e.g., the optimizer 202). In some examples of the method 1000, the administrator provides feedback via the rules viewer of the example fifth screen 700 of FIG. 7 by editing one or more the available or active rules (e.g., via the rules editor 710). In adjusting the rules, the example method 1000 provides for the administrator to facilitate automated suggestions and improvements to the exam distribution process. Such administrator-initiated revisions are detected by the optimizer 220 in measuring, analyzing, developing, and implementing efficiency improvements with respect to the one or more revised rules as well as the workflow process in general. The example method 1000 ends at block 1020 with the administrator continuing to monitor the workflow distribution in view the revised rules.

In operation, the example method 1000 provides for the administrator to review the current workflow status of pending exams as well as real-time and historical operational metrics associated with the workflow. Based on a review of the exam distribution status and review and patterns and trends observable from the metrics, the administrator may wish to revise the automatic allocation of exams by the exam distributor 102. The example method 1000 provides for the administrator to re-distribute exams among radiologists as a discrete incident or by adjusting the rules used by the exam distributor in automatically allocating exams. Further, the example method 1000 facilitates incorporation of the administrator's feedback associated with, for example, revisions to the load-balancing rules, into the automated monitoring and optimizations performed by the optimizer.

FIG. 11 illustrates a flow diagram of an example method 1100 for optimizing exam distribution by the exam distributor 102. The example method 1100 can be implemented at least partly by, for example, the optimizer 220 of the exam distributor 102 (FIGS. 2, 9). The example method 1110 beings at block 1102 with the distributing one or more exams using the load-balancing rules. For example, the exam distributor 102, including the allocation manager 212, distributes exams using the load-balancing rules defined by the rules creator 210.

At block 1104, the current workflow statuses of the exams requiring review are tracked by, for example, the optimizer 220. Additionally, at block 1106, the optimizer 220 retrieves historical data associated with the allocation and assignment of exams by the exam distributor 102. The historical data can include, for example, numbers of exams distributed per month, revenue generated, examiner availability history, etc. The historical data can be retrieved from the database 216 of FIG. 2.

At block 1108, the calculator 218 of the exam distributor of FIG. 2 calculates workflow metrics based on data associated with the current workflow statuses (block 1104) and the historical data (block 1106). Such metrics relate to, for example, actual and target exam review efficiency rates. Such metrics can also relate to, for example, institutional and/or clinical goals, strategies, and resources.

The example method 1100 includes identifying trends based on the workflow metrics calculated at block 1106. For example, the optimizer 220 employs data mining techniques, statistical analysis, or other analytical tools to identify trends inherent in the current and historical data associated with the distribution and review of exams. Such trends include, for example, patterns with respect to radiologists meeting or not meeting allocated exam review times, frequently received types of exams, radiologists with the heaviest and lights work queues, patterns in radiologist availability, patterns in radiologist exam acceptance histories, etc.

At block 1112, the optimizer 220 evaluates user feedback received via the user input module 206 of FIG. 2. The user input is received via the user interface 126 (e.g., the administrator or examiner interfaces 202, 204*a-n*). For example, via the example assignment tool described in connection with the example third screen 500 of FIG. 3, the administrator can enter an input to redistribute the allocation of an exam among radiologists. Also, via the rules viewer of the example fifth screen 700, the administrator can edit one or more rules used by the exam distributor 102 in distributing exams. In further examples, a radiologist can update the examiner availability indicator 322 (FIG. 3) via the examiner interface 204*a*. As part of the example method 1100 for optimizing exam distribution, the optimizer 220 detects and evaluates user feedback with respect to the allocation and assignment of exams. For example, the optimizer 220 can detect repeated re-distribution of exams associated with certain attributes from a first radiologist to a second radiologist by the administrator via the exam assignment tool of FIG. 5. The optimizer also detects repeated rejections of allocated exams by the radiologist and evaluate whether the administrator has taken any action to override the rejections.

In reviewing data, identifying trends, and evaluating user feedback as described in connection with blocks 1104-1112, the optimizer 220 performs analysis in view of efficiency of the workflow process implemented by the exam distributor 102. In light of such an analysis, the optimizer 220 detects one or more areas of inefficiencies that could be addressed to increase workflow efficiency. At block 1114, a decision is made by the optimizer 220 regarding whether to update one or more of the load-balancing rules defined by the rules creator 210 based on identified inefficiencies detected from the metrics, trends, and feedback considered at blocks 1104-1112. The optimizer 220 uses, process improvement models, including, but not limited to, Six Sigma, lean optimization, multivariable testing, and/or some combination of global optimization models to identify areas for improvements with respect to exam distribution based on the analytical data analysis.

If a decision is made by the optimizer 220 to update one or more of the load-balancing rules, the one or more rules and/or rule parameters are adjusted by the optimizer 220 at block 1116. For example, the optimizer adjusts the weight given to a rule or the frequency in which the rule is implemented by the exam distributor 102. The optimizer 220 can enact other adjustments to the rule parameters directed toward improving exam distribution efficiency. As described above in connection with FIG. 9, the optimizer 220 considers the impact of the rule adjustments across the exam distribution process associated with radiology network, institution, or group of institutions.

In some examples, the updated rules are automatically implemented by the exam distributor 102. In other examples, the example method 1100 optionally includes presenting the proposed updated rule(s) to the administrator for review, as shown at block 1118. In such examples, the administrator can approve or reject the updated rule(s), thus, control whether the updated rule(s) are implemented. Thus, the example method 1100 optionally provides for administrative control of exam distribution outcomes.

At block 1120, a decision is made whether to distribute additional exams. If the exam distributor 102 is to distribute additional exams, the distribution is based on the updated rule(s) provided by the optimizer 220. Thus, the example method 1100 provides for dynamic adjustment of the load-balancing rules during operation of the exam distributor 102 in response to ongoing monitoring of current and historical workflow data. As the exam distributor distributes the additional exams using the updated rule(s), the optimization method of FIG. 11 repeats to continuously monitor the efficiency of the exam distributor 102. For example, the calculator 218 generates updated metrics in view of the impact of the updated rule(s) on the current workflow data and the optimizer 220 evaluates the efficiency improvements, lack of improvements, and/or negative effects of the updated rules throughout the workflow process and considers whether to make further adjustments.

In some examples, if the optimizer 220 determines that a rules adjustment would not increase the efficiency of the workflow process or might have a negative effect on one or more aspects of the workflow process, the optimizer 220 refrains from adjusting the one or more rules. If, at block 1114, the optimizer 220 determines that, based on the data analysis, no adjustments to one or more rules should be performed, the example method 1110 continues to block 1120, where a decision is made to distribute additional exams. If a decision is made at block 1120 to distribute additional exams, the example method 1100 repeats. The optimizer 220 continuously monitors the efficiency of exam distributor 102 and makes real-time decisions with respect to adjusting the rules during operation of the exam distributor 102. If a decision is made at block 1120 not to distribute additional exams, the example method 1100 ends at block 1122 with the optimizer 220 continuing to monitor the status of the workflow process.

In operation, the example method 1100 provides for optimization of the exam distribution process in view of real-time and historical data as well as user feedback. In performing a data-driven analysis with respect to the efficiency of workflow process, the example method 1100 dynamically responds to changes inherently reflected in the collected data as well as the influence of user inputs and external variables. The example method 1100 can be continuously implemented during operation of the exam distributor 102 with a goal of amassing statistics and performance measures that can be used to further analyze and direct the behavior of the exam distributor 102. Additionally, the example method 1100 can integrate user feedback. Further, the example method 1100 can supplement and respond to the administrative review described in connection with the example method 1000 of FIG. 10. In certain examples, the example method 1100 provides for a comprehensive, data-driven approach to increasing exam distribution and workflow management.

Figure 12:
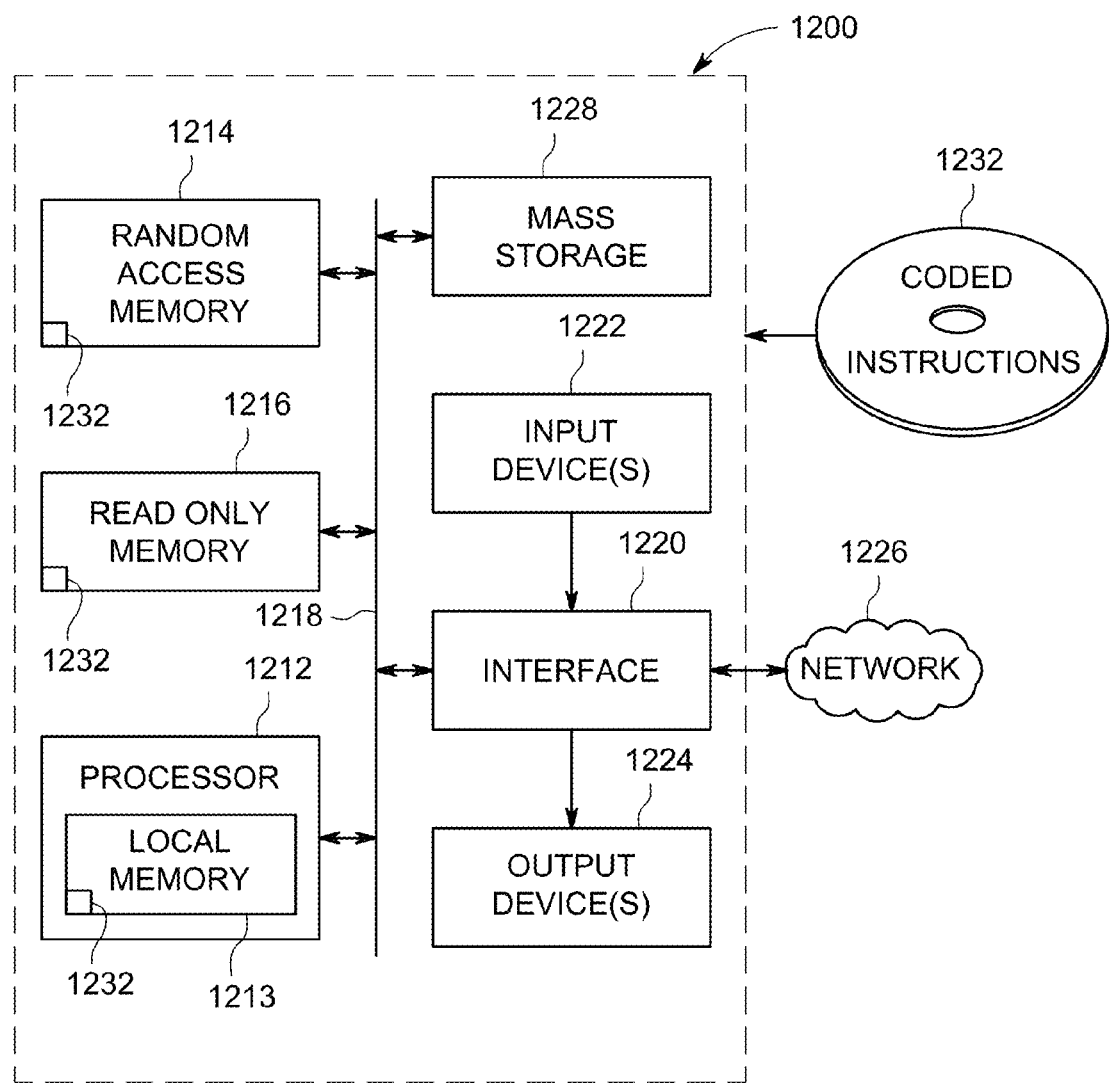
FIG. 12 shows a block diagram of an example processor system that can be used to implement systems and methods described herein.

FIG. 12 is a block diagram of an example processor platform 1200 capable of executing the instructions of FIGS. 10 and 11 to implement the exam distributor 102 of FIG. 1. The processor platform 1200 can be, for example, a server, a personal computer, a mobile device (e.g., a cell phone, a smart phone, a tablet such as an IPAD™) a personal digital assistant (PDA), an Internet appliance, or any other type of computing device.

The processor platform 1200 of the illustrated example includes a processor 1212. The processor 1212 of the illustrated example is hardware. For example, the processor 1212 can be implemented by one or more integrated circuits, logic circuits, microprocessors or controllers from any desired family or manufacturer.

The processor 1212 of the illustrated example includes a local memory 1213 (e.g., a cache). The processor 1212 of the illustrated example is in communication with a main memory including a volatile memory 1214 and a non-volatile memory 1216 via a bus 1218. The volatile memory 1214 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1216 can be implemented by flash memory and/or any other desired type of memory device. Access to the main memory 1214, 1216 is controlled by a memory controller.

The processor platform 1200 of the illustrated example also includes an interface circuit 1220. The interface circuit 1220 can be implemented by any type of interface standard, such as an Ethernet interface, a universal serial bus (USB), and/or a PCI express interface.

In the illustrated example, one or more input devices 1222 are connected to the interface circuit 1220. The input device(s) 1222 permit(s) a user to enter data and commands into the processor 1212. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1224 are also connected to the interface circuit 1220 of the illustrated example. The output devices 1224 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 1220 of the illustrated example, thus, typically includes a graphics driver card, a graphics driver chip or a graphics driver processor.

The interface circuit 1220 of the illustrated example also includes a communication device such as a transmitter, a receiver, a transceiver, a modem and/or network interface card to facilitate exchange of data with external machines (e.g., computing devices of any kind) via a network 1226 (e.g., an Ethernet connection, a digital subscriber line (DSL), a telephone line, coaxial cable, a cellular telephone system, etc.).

The processor platform 1200 of the illustrated example also includes one or more mass storage devices 1228 for storing software and/or data. Examples of such mass storage devices 1228 include floppy disk drives, hard drive disks, compact disk drives, Blu-ray disk drives, RAID systems, and digital versatile disk (DVD) drives.

The coded instructions 1232 of FIGS. 10 and 11 can be stored in the mass storage device 1228, in the volatile memory 1214, in the non-volatile memory 1216, and/or on a removable tangible computer readable storage medium such as a CD or DVD.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A system to manage a radiologist workflow, the system comprising a processor, the processor configured to implement:
    a first interface to monitor a distribution status of at least one medical exam, wherein the medical exam is to be at least one of automatically allocated or assigned to an examiner work queue based on one or more rules, the examiner work queue to be displayed via a second interface, the distribution status to update in response to a first user input received via a surface of the second interface;
    a third interface to view at least one metric associated with distribution of the at least one medical exam;
    an assignment tool to be displayed via the first interface, the assignment tool to receive a second user input via the first interface for the automatic allocation or assignment of the medical exam and to distribute the medical exam to an examiner work queue based on the second user input, the second user input including an adjustment to the automatic allocation or assignment based on the first user input; and
    a rules viewer to be displayed via a fourth interface, wherein the rules viewer is to facilitate configuration of the one or more rules, the rules viewer to automatically update the one or more rules based on the second user input and a trend, the trend calculated based on the distribution status, the at least one metric, or the assignment, one or more of the first interface, the second interface, the third interface, or the fourth interface to be automatically updated based on the update of the one or more rules.

2. The system of claim 1, further comprising an exam alert to be displayed via the third interface, the exam alert to indicate a time limit for examination of the medical exam.

3. The system of claim 2, wherein the assignment is based on the exam alert.

4. The system of claim 1, wherein the distribution status is to update in response to acceptance or rejection of the assignment from the examiner work queue via the first user input.

5. The system of claim 4, wherein the second user input is a selection to override the rejection of the assignment, the assignment tool to distribute the medical exam based on the selection.

6. The system of claim 1, wherein the at least one metric is associated with an efficiency of review of the medical exam assigned to the examiner work queue, and wherein the rules viewer is to update the one or more rules based on the efficiency.

7. The system of claim 1, wherein the rules viewer is to monitor the at least one metric, the rules viewer to automatically update the one or more rules based on the monitoring.

8. The system of claim 1, wherein the examiner work queue is a first examiner work queue and the assignment tool is to facilitate the assignment of the medical exam from the first examiner work queue to a second examiner work queue, the first examiner work queue associated with a first examiner and the second examiner work queue associated with a second examiner.

9. The system of claim 1, wherein the at least one metric is representative of a tracking of the distribution status over a period of time.

10. The system of claim 1, further comprising an examiner scorecard to be displayed via the first interface, wherein the assignment is based on the examiner scorecard.

11. The system of claim 1, wherein the rules viewer to is display the updated rule via the fourth interface prior to implementation of the updated rule.

12. The system of claim 1, further comprising an examiner availability indicator to be displayed via the first interface, the rules viewer to facilitate configuration of the one or more rules based on the examiner availability indicator.

13. The system of claim 1, wherein the rules viewer is to dynamically optimize the one or more rules based on a tracking of the at least one metric, and wherein the optimization is to adjust the distribution of the at least one medical exam between a first radiologist and a second radiologist.

14. A method to manage a radiologist workflow, the method comprising:
    monitoring, by executing a first instruction with a processor, a distribution status of at least one medical exam via a first interface, wherein the medical exam is to be at least one of automatically allocated or assigned to an examiner work queue based on one or more rules, the examiner work queue to be displayed via second interface, the distribution status to update in response to a first user input received via a surface of the second interface;
    displaying, by executing a second instruction with the processor, at least one metric associated with the distribution of the at least one medical exam via a third interface;
    distributing, by executing a fourth instruction with the processor, the medical exam to an examiner work queue based on a second user input for the automatic allocation or assignment of the medical exam, the second user input received via the first interface, the second user input including an adjustment to the automatic allocation or assignment based on the first user input;
    facilitating, by executing a fourth instruction with the processor, a configuration of the one or more rules based on the distribution status, the at least one metric, or the assignment via the first interface;
    automatically updating, by executing a fifth instruction with the processor, the one or more rules based on the second user input and a trend, the trend calculated based on the distribution status, the at least one metric, or the assignment; and
    automatically updating, by executing a sixth instruction with the processor, one or more of the first interface, the second interface, or the third interface based on the update of the one or more rules.

15. The method of claim 14, further comprising distributing the medical exam by overriding a rejection of the assignment from the examiner work queue.

16. The method of claim 14, further comprising:
    monitoring the at least one metric; and
    automatically updating the one or more rules based on the monitoring.

17. The method of claim 14, displaying an exam alert via the third interface, the exam alert to indicate a time limit for examination of the medical exam.

18. The method of claim 14, further comprising:
    displaying an examiner scorecard via the first interface; and distributing the medical exam based on the examiner scorecard.

19. A machine readable storage device or disc, containing instructions thereon, which when read cause a machine to at least:
monitor a distribution status of at least one medical exam via a first interface, wherein the medical exam is to be at least one of automatically allocated or assigned to an examiner work queue based on one or more rules, the examiner work queue to be displayed via second interface, the distribution status to update in response to a first user input received via a surface of the second interface;
display at least one metric associated with the distribution of the at least one medical exam via a third interface;
distribute the medical exam to an examiner work queue based on a second user input for the automatic allocation or assignment of the medical exam, the user input received via the first interface, the second user input including an adjustment to the automatic allocation or assignment based on the first user input;
facilitate a configuration of the one or more rules based on the distribution status, the at least one metric, or the assignment via the first interface;
automatically update the one or more rules based on the second user input and a trend, the trend calculated based on the distribution status, the at least one metric, or the assignment; and
automatically update one or more of the first interface, the second interface, or the third based on the update of the one or more rules.

20. The machine readable storage device or storage disc of claim 19, wherein the instructions cause the machine to display an exam via the third interface, the exam alert to indicate a time limit for examination of the medical exam.

21. The machine readable storage device or storage disc of claim 19, wherein the instructions cause the machine to track the distribution status over a period of time, the at least one metric representative of the tracking.

* * * * *